United States Patent
Terry

(10) Patent No.: US 10,342,952 B2
(45) Date of Patent: *Jul. 9, 2019

(54) CATHETER ASSEMBLY/PACKAGE UTILIZING A HYDRATING/HYDROGEL SLEEVE AND A FOIL OUTER LAYER AND METHOD OF MAKING AND USING THE SAME

(71) Applicant: C. R. Bard, Inc., Murray Hill, NJ (US)

(72) Inventor: Richard Terry, Conyers, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/669,697

(22) Filed: Aug. 4, 2017

(65) Prior Publication Data

US 2017/0326334 A1    Nov. 16, 2017

Related U.S. Application Data

(63) Continuation of application No. 14/707,954, filed on May 8, 2015, now Pat. No. 9,731,093, which is a
(Continued)

(51) Int. Cl.
*A61F 2/04*     (2013.01)
*A61M 25/00*   (2006.01)
(Continued)

(52) U.S. Cl.
CPC ........... *A61M 25/002* (2013.01); *A61F 2/042* (2013.01); *A61M 25/0017* (2013.01);
(Continued)

(58) Field of Classification Search
CPC ............ A61M 25/002; A61M 25/0045; A61M 25/0017; A61M 2025/0046;
(Continued)

(56) References Cited

U.S. PATENT DOCUMENTS

| 1,888,349 A | 11/1932 | Jacoby |
| 2,912,981 A | 11/1959 | Keough |

(Continued)

FOREIGN PATENT DOCUMENTS

| CA | 2770300 A1 | 2/2011 |
| CA | 2769026 C | 4/2015 |

(Continued)

OTHER PUBLICATIONS

"Tripartite Biocompatibility Guidance for Medical Devices," DSMA (Apr. 24, 1987).
(Continued)

*Primary Examiner* — Chun Hoi Cheung
(74) *Attorney, Agent, or Firm* — Rutan & Tucker, LLP

(57) ABSTRACT

A catheter assembly includes a catheter, a coating, a fluid containing sleeve, and a container. The catheter may include one or more distal drainage openings. The coating may be disposed on an outer surface of the catheter. The fluid containing sleeve may have an outer foil layer and be configured for positioning over the outer surface of the catheter to maintain the coating in a hydrated state. The container may enclose the catheter and the fluid containing sleeve. Substantially all fluid in the container may be disposed in the fluid containing sleeve.

23 Claims, 10 Drawing Sheets

Related U.S. Application Data continuation of application No. 13/582,698, filed as application No. PCT/US2011/026681 on Mar. 1, 2011, now Pat. No. 9,033,149.

(60) Provisional application No. 61/310,535, filed on Mar. 4, 2010.

(51) Int. Cl.
 *B65D 65/38* (2006.01)
 *B65D 77/04* (2006.01)
 *B65D 81/22* (2006.01)

(52) U.S. Cl.
 CPC ......... *A61M 25/0045* (2013.01); *B65D 65/38* (2013.01); *B65D 77/04* (2013.01); *B65D 81/22* (2013.01); *A61M 2025/0046* (2013.01); *A61M 2025/0047* (2013.01)

(58) Field of Classification Search
 CPC ............ A61M 2025/0047; A61F 2/042; B65D 65/38; B65D 77/04; B65D 81/22
 USPC ........ 206/571, 363, 364, 210; 604/265, 172, 604/544
 See application file for complete search history.

(56) References Cited

U.S. PATENT DOCUMENTS

| | | |
|---|---|---|
| 2,919,697 A | 1/1960 | Kim |
| 3,173,566 A | 3/1965 | Talbert |
| 3,344,791 A | 10/1967 | Foderick |
| 3,345,988 A * | 10/1967 | Vitello ............... A61M 25/002 206/364 |
| 3,556,294 A * | 1/1971 | Walck, III ........... A61M 25/002 206/210 |
| 3,556,874 A | 1/1971 | McClain |
| 3,566,874 A | 3/1971 | Shepherd et al. |
| 3,648,704 A | 3/1972 | Jackson |
| 3,695,921 A | 10/1972 | Shepherd et al. |
| 3,699,964 A | 10/1972 | Ericson |
| 3,726,281 A | 4/1973 | Norton et al. |
| 3,794,042 A | 2/1974 | De Klotz et al. |
| 3,802,987 A | 4/1974 | Noll |
| 3,835,992 A | 9/1974 | Adams, IV |
| 3,854,483 A | 12/1974 | Powers |
| 3,861,395 A | 1/1975 | Taniguchi |
| 3,894,540 A | 7/1975 | Bonner, Jr. |
| 3,898,993 A | 8/1975 | Taniguchi |
| 3,934,721 A | 1/1976 | Juster et al. |
| 3,967,728 A | 7/1976 | Gordon et al. |
| 4,026,296 A | 5/1977 | Stoy et al. |
| 4,051,849 A | 10/1977 | Poncy et al. |
| 4,055,682 A | 10/1977 | Merrill |
| 4,062,363 A | 12/1977 | Bonner, Jr. |
| 4,069,359 A | 1/1978 | DeMarse et al. |
| 4,091,922 A | 5/1978 | Egler |
| 4,140,127 A | 2/1979 | Cianci et al. |
| 4,198,983 A | 4/1980 | Becker et al. |
| 4,230,115 A | 10/1980 | Walz, Jr. et al. |
| 4,245,639 A | 1/1981 | La Rosa |
| 4,246,909 A | 1/1981 | Wu et al. |
| 4,269,310 A | 5/1981 | Uson et al. |
| 4,306,557 A | 12/1981 | North |
| 4,350,161 A | 9/1982 | Davis, Jr. |
| 4,351,333 A | 9/1982 | Lazarus et al. |
| 4,366,901 A | 1/1983 | Short |
| 4,392,848 A | 7/1983 | Lucas et al. |
| 4,411,648 A | 10/1983 | Davis et al. |
| 4,515,593 A | 5/1985 | Norton |
| 4,517,971 A | 5/1985 | Sorbonne |
| 4,560,382 A | 12/1985 | Isono et al. |
| 4,571,241 A | 2/1986 | Christopher |
| 4,585,666 A | 4/1986 | Lambert |
| 4,597,765 A | 7/1986 | Klatt |
| 4,607,746 A | 8/1986 | Stinnette |
| 4,610,670 A | 9/1986 | Spencer |
| 4,619,642 A | 10/1986 | Spencer |
| 4,681,572 A | 7/1987 | Tokarz et al. |
| 4,692,154 A | 9/1987 | Singery et al. |
| 4,696,672 A | 9/1987 | Mochizuki et al. |
| 4,704,102 A | 11/1987 | Guthery |
| 4,723,946 A | 2/1988 | Kay |
| 4,738,667 A | 4/1988 | Galloway |
| 4,754,877 A | 7/1988 | Johansson et al. |
| 4,759,753 A | 7/1988 | Schneider et al. |
| 4,762,128 A | 8/1988 | Rosenbluth |
| 4,773,901 A | 9/1988 | Norton |
| 4,784,651 A | 11/1988 | Hickey et al. |
| 4,811,847 A | 3/1989 | Reif et al. |
| 4,838,876 A | 6/1989 | Wong et al. |
| 4,886,508 A | 12/1989 | Washington |
| 4,888,005 A | 12/1989 | Dingeman et al. |
| 4,893,623 A | 1/1990 | Rosenbluth |
| 4,932,938 A | 6/1990 | Goldberg et al. |
| 4,957,487 A | 9/1990 | Gerow |
| 4,997,426 A | 3/1991 | Dingeman et al. |
| 5,007,897 A | 4/1991 | Kalb et al. |
| 5,045,078 A | 9/1991 | Asta |
| 5,077,352 A | 12/1991 | Elton |
| 5,087,252 A | 2/1992 | Denard |
| 5,098,379 A | 3/1992 | Conway et al. |
| 5,100,396 A | 3/1992 | Zamierowski |
| 5,137,671 A | 8/1992 | Conway et al. |
| 5,147,341 A | 9/1992 | Starke et al. |
| 5,174,290 A | 12/1992 | Fiddian-Green |
| 5,179,174 A | 1/1993 | Elton |
| 5,180,591 A | 1/1993 | Magruder et al. |
| 5,186,172 A | 2/1993 | Fiddian-Green |
| 5,188,596 A | 2/1993 | Condon et al. |
| 5,201,724 A | 4/1993 | Hukins et al. |
| 5,209,726 A | 5/1993 | Goosen |
| 5,209,728 A | 5/1993 | Kraus et al. |
| 5,224,953 A | 7/1993 | Morgentaler |
| 5,226,530 A * | 7/1993 | Golden ............... A61M 25/002 206/210 |
| 5,234,411 A | 8/1993 | Vaillancourt |
| 5,236,422 A | 8/1993 | Eplett, Jr. |
| 5,242,398 A | 9/1993 | Knoll et al. |
| 5,242,428 A | 9/1993 | Palestrant |
| 5,261,896 A | 11/1993 | Conway et al. |
| 5,269,755 A | 12/1993 | Bodicky |
| 5,269,770 A | 12/1993 | Conway et al. |
| 5,282,795 A | 2/1994 | Finney |
| 5,352,182 A | 10/1994 | Kalb et al. |
| 5,360,402 A | 11/1994 | Conway et al. |
| 5,370,899 A | 12/1994 | Conway et al. |
| 5,415,165 A | 5/1995 | Fiddian-Green |
| 5,417,666 A | 5/1995 | Coulter |
| 5,433,713 A | 7/1995 | Trotta |
| 5,445,626 A | 8/1995 | Gigante et al. |
| 5,447,231 A | 9/1995 | Kastenhofer |
| 5,454,798 A | 10/1995 | Kubalak et al. |
| 5,456,251 A | 10/1995 | Fiddian-Green |
| 5,466,229 A | 11/1995 | Elson et al. |
| 5,476,434 A | 12/1995 | Kalb et al. |
| 5,482,740 A | 1/1996 | Conway et al. |
| 5,501,669 A | 3/1996 | Conway et al. |
| 5,509,889 A | 4/1996 | Kalb et al. |
| 5,514,112 A | 5/1996 | Chu et al. |
| 5,520,636 A | 5/1996 | Korth et al. |
| 5,531,715 A | 7/1996 | Engelson et al. |
| 5,531,717 A | 7/1996 | Roberto et al. |
| 5,536,258 A | 7/1996 | Folden |
| 5,558,900 A | 9/1996 | Fan et al. |
| 5,569,219 A | 10/1996 | Hakki et al. |
| 5,582,599 A | 12/1996 | Daneshvar |
| 5,591,292 A | 1/1997 | Blomqvist |
| 5,599,321 A | 2/1997 | Conway et al. |
| 5,601,537 A | 2/1997 | Frassica |
| 5,607,417 A | 3/1997 | Batich et al. |
| 5,616,126 A | 4/1997 | Malekmehr et al. |
| 5,624,395 A | 4/1997 | Mikhail et al. |
| 5,653,700 A | 8/1997 | Byrne et al. |

(56) References Cited

U.S. PATENT DOCUMENTS

| | | |
|---|---|---|
| 5,670,111 A | 9/1997 | Conway et al. |
| 5,688,516 A | 11/1997 | Raad et al. |
| 5,704,353 A | 1/1998 | Kalb et al. |
| 5,707,357 A | 1/1998 | Mikhail et al. |
| 5,711,841 A | 1/1998 | Jaker |
| 5,749,826 A | 5/1998 | Faulkner |
| 5,779,670 A | 7/1998 | Bidwell et al. |
| 5,782,808 A | 7/1998 | Folden |
| 5,785,694 A | 7/1998 | Cohen |
| 5,788,687 A | 8/1998 | Batich et al. |
| 5,800,339 A | 9/1998 | Salama |
| 5,817,067 A | 10/1998 | Tsukada et al. |
| 5,820,583 A | 10/1998 | Demopulos et al. |
| 5,840,151 A | 11/1998 | Munsch |
| 5,848,691 A | 12/1998 | Morris et al. |
| 5,853,518 A | 12/1998 | Utas et al. |
| 5,871,475 A | 2/1999 | Frassica |
| 5,895,374 A | 4/1999 | Rodsten et al. |
| 5,897,535 A | 4/1999 | Feliziani et al. |
| 5,941,856 A | 8/1999 | Kovacs et al. |
| 5,971,954 A | 10/1999 | Conway et al. |
| 5,980,483 A | 11/1999 | Dimitri et al. |
| 5,989,230 A | 11/1999 | Frassica |
| 6,004,305 A | 12/1999 | Hursman et al. |
| 6,007,521 A | 12/1999 | Bidwell et al. |
| 6,024,751 A | 2/2000 | Lovato et al. |
| 6,050,934 A | 4/2000 | Mikhail et al. |
| 6,053,905 A | 4/2000 | Daignault, Jr. et al. |
| 6,056,715 A | 5/2000 | Demopulos et al. |
| 6,059,107 A | 5/2000 | Nosted et al. |
| 6,063,063 A | 5/2000 | Harboe et al. |
| 6,090,075 A | 7/2000 | House |
| 6,156,049 A | 12/2000 | Lovato et al. |
| 6,162,201 A | 12/2000 | Cohen et al. |
| 6,183,461 B1 | 2/2001 | Matsuura et al. |
| 6,186,990 B1 | 2/2001 | Chen et al. |
| 6,190,353 B1 | 2/2001 | Makower et al. |
| 6,210,394 B1 | 4/2001 | Demopulos et al. |
| 6,217,569 B1 | 4/2001 | Fiore |
| 6,221,056 B1 | 4/2001 | Silverman |
| 6,238,383 B1 | 5/2001 | Karram et al. |
| 6,254,570 B1 | 7/2001 | Rutner et al. |
| 6,254,582 B1 | 7/2001 | O'Donnell et al. |
| 6,254,585 B1 | 7/2001 | Demopulos et al. |
| 6,261,279 B1 | 7/2001 | Demopulos et al. |
| 6,293,923 B1 | 9/2001 | Yachia et al. |
| 6,299,598 B1 | 10/2001 | Bander |
| 6,306,422 B1 | 10/2001 | Batich et al. |
| 6,329,488 B1 | 12/2001 | Terry et al. |
| 6,340,359 B1 | 1/2002 | Silverman |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Israelsson et al. |
| 6,458,867 B1 | 10/2002 | Wang et al. |
| 6,468,245 B2 | 10/2002 | Alexandersen et al. |
| 6,485,476 B1 | 11/2002 | von Dyck et al. |
| 6,544,240 B1 | 4/2003 | Borodulin et al. |
| 6,578,709 B1 | 6/2003 | Kavanagh et al. |
| 6,582,401 B1 | 6/2003 | Windheuser et al. |
| 6,602,244 B2 | 8/2003 | Kavanagh et al. |
| 6,613,342 B2 | 9/2003 | Aoki |
| 6,626,888 B1 | 9/2003 | Conway et al. |
| 6,629,969 B2 | 10/2003 | Chan et al. |
| 6,634,498 B2 | 10/2003 | Kayerod et al. |
| 6,638,269 B2 | 10/2003 | Wilcox |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,695,831 B1 | 2/2004 | Tsukada et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,730,113 B2 | 5/2004 | Eckhardt et al. |
| 6,736,805 B2 | 5/2004 | Israelsson et al. |
| 6,746,421 B2 | 6/2004 | Yachia et al. |
| 6,783,520 B1 | 8/2004 | Candray et al. |
| D496,266 S | 9/2004 | Nestenborg et al. |
| 6,824,532 B2 | 11/2004 | Gillis et al. |
| 6,835,183 B2 | 12/2004 | Lennox et al. |
| 6,840,379 B2 | 1/2005 | Franks-Farah et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,887,230 B2 | 5/2005 | Kubalak et al. |
| 6,889,740 B1 | 5/2005 | Globensky et al. |
| 6,918,924 B2 | 7/2005 | Lasheras et al. |
| 6,926,708 B1 | 8/2005 | Franks-Farah et al. |
| 6,939,339 B1 | 9/2005 | Axexandersen et al. |
| 6,941,171 B2 | 9/2005 | Mann et al. |
| 6,942,634 B2 | 9/2005 | Odland |
| 6,945,957 B2 | 9/2005 | Freyman |
| 6,949,598 B2 | 9/2005 | Terry |
| 7,001,370 B2 | 2/2006 | Kubalak et al. |
| 7,048,717 B1 | 5/2006 | Frassica |
| 7,059,330 B1 | 6/2006 | Makower et al. |
| 7,066,912 B2 | 6/2006 | Nestenborg et al. |
| 7,087,041 B2 | 8/2006 | von Dyck et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,195,608 B2 | 3/2007 | Burnett |
| 7,244,242 B2 | 7/2007 | Freyman |
| 7,250,043 B2 | 7/2007 | Chan et al. |
| 7,255,687 B2 | 8/2007 | Huang et al. |
| 7,270,647 B2 | 9/2007 | Karpowicz et al. |
| 7,294,117 B2 | 11/2007 | Provost-tine et al. |
| 7,311,690 B2 | 12/2007 | Burnett |
| 7,311,698 B2 | 12/2007 | Tanghoj et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,537,589 B2 | 5/2009 | Tsukada et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosier et al. |
| 7,662,146 B2 | 2/2010 | House |
| 7,682,353 B2 | 3/2010 | Tanghoj et al. |
| 7,770,726 B2 | 8/2010 | Murray et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,066,693 B2 | 11/2011 | Tanghoj et al. |
| 8,177,774 B2 | 5/2012 | House |
| 8,181,778 B1 | 5/2012 | Van Groningen et al. |
| 8,205,745 B2 | 6/2012 | Murray et al. |
| 8,328,792 B2 | 12/2012 | Nishtala et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,998,882 B2 | 4/2015 | Knapp et al. |

(56) References Cited

U.S. PATENT DOCUMENTS

| | | |
|---|---|---|
| 9,033,149 B2 | 5/2015 | Terry |
| 9,114,227 B2 | 8/2015 | Blanchard |
| 9,694,113 B2 | 7/2017 | Knapp et al. |
| 9,731,093 B2 | 8/2017 | Terry |
| 9,821,139 B2 | 11/2017 | Carleo |
| 10,149,961 B2 | 12/2018 | Carleo |
| 2001/0001443 A1 | 5/2001 | Kayerod et al. |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |
| 2002/0037943 A1 | 3/2002 | Madsen |
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0094322 A1 | 7/2002 | Lawson et al. |
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0132013 A1 | 9/2002 | Moulis |
| 2002/0133130 A1 | 9/2002 | Wilcox |
| 2002/0156440 A1 | 10/2002 | Israelsson et al. |
| 2002/0165427 A1 | 11/2002 | Yachia et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0130646 A1 | 7/2003 | Kubalak et al. |
| 2003/0132307 A1 | 7/2003 | Park |
| 2003/0135200 A1 | 7/2003 | Byrne |
| 2003/0163079 A1 | 8/2003 | Burnett |
| 2003/0195478 A1 | 10/2003 | Russo |
| 2003/0225392 A1 | 12/2003 | McMichael et al. |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0074794 A1 | 4/2004 | Conway et al. |
| 2004/0116551 A1 | 6/2004 | Terry |
| 2004/0127848 A1 | 7/2004 | Freyman |
| 2004/0133156 A1 | 7/2004 | Diaz et al. |
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1 | 9/2004 | Feneley |
| 2004/0243104 A1 | 12/2004 | Seddon |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0003118 A1 | 1/2005 | Takala |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0059990 A1 | 3/2005 | Ayala et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0283136 A1 | 12/2005 | Skarda |
| 2006/0025753 A1 | 2/2006 | Kubalak |
| 2006/0027854 A1 | 2/2006 | Kim et al. |
| 2006/0030864 A1 | 2/2006 | Kennedy et al. |
| 2006/0036208 A1 | 2/2006 | Burnett |
| 2006/0041246 A1 | 2/2006 | Provost-tine et al. |
| 2006/0054557 A1 | 3/2006 | Hori et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0100511 A1 | 5/2006 | Eriksen |
| 2006/0122566 A1 | 6/2006 | Huang et al. |
| 2006/0122568 A1 | 6/2006 | Elson et al. |
| 2006/0163097 A1 | 7/2006 | Murray et al. |
| 2006/0172096 A1 | 8/2006 | Kyle et al. |
| 2006/0184112 A1 | 8/2006 | Horn et al. |
| 2006/0184145 A1 | 8/2006 | Ciok et al. |
| 2006/0196783 A1 | 9/2006 | Bruun et al. |
| 2006/0200079 A1 | 9/2006 | Magnusson |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1 | 12/2006 | State et al. |
| 2006/0293642 A1 | 12/2006 | Israelsson et al. |
| 2007/0005041 A1 | 1/2007 | Frassica et al. |
| 2007/0010798 A1 | 1/2007 | Stoller et al. |
| 2007/0016169 A1 | 1/2007 | Utas et al. |
| 2007/0049879 A1 | 3/2007 | Gutierrez |
| 2007/0066963 A1 | 3/2007 | Tanghoj |
| 2007/0106233 A1 | 5/2007 | Huang et al. |
| 2007/0112327 A1 | 5/2007 | Yun et al. |
| 2007/0149929 A1 | 6/2007 | Utas et al. |
| 2007/0197957 A1 | 8/2007 | Hunter et al. |
| 2007/0225635 A1 | 9/2007 | Lynn |
| 2007/0225649 A1 | 9/2007 | House |
| 2007/0225687 A1 | 9/2007 | House |
| 2007/0244449 A1 | 10/2007 | Najafi et al. |
| 2007/0289887 A1 | 12/2007 | Murray et al. |
| 2008/0006554 A1 | 1/2008 | Duffy et al. |
| 2008/0015518 A1 | 1/2008 | Huang et al. |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1 | 2/2008 | Ziegler et al. |
| 2008/0051762 A1 | 2/2008 | Tsukada et al. |
| 2008/0051763 A1 | 2/2008 | Frojd |
| 2008/0077099 A1 | 3/2008 | House |
| 2008/0082051 A1 | 4/2008 | Miller et al. |
| 2008/0085949 A1 | 4/2008 | McGhee |
| 2008/0091145 A1 | 4/2008 | House |
| 2008/0097362 A1 | 4/2008 | Mosler et al. |
| 2008/0097394 A1 | 4/2008 | Lampropoulos et al. |
| 2008/0097411 A1 | 4/2008 | House |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172042 A1 | 7/2008 | House |
| 2008/0179208 A1 | 7/2008 | Murray et al. |
| 2008/0200907 A1 | 8/2008 | Nestenborg |
| 2008/0243091 A1 | 10/2008 | Humphreys et al. |

(56) References Cited

U.S. PATENT DOCUMENTS

| | | |
|---|---|---|
| 2008/0249467 A1 | 10/2008 | Burnett et al. |
| 2008/0249482 A1 | 10/2008 | Erez |
| 2008/0275463 A1 | 11/2008 | High |
| 2009/0024111 A1 | 1/2009 | Borodulin et al. |
| 2009/0048537 A1 | 2/2009 | Lydon et al. |
| 2009/0054876 A1 | 2/2009 | Borodulin et al. |
| 2009/0065605 A1 | 3/2009 | Roche et al. |
| 2009/0071851 A1 | 3/2009 | Maki et al. |
| 2009/0099532 A1 | 4/2009 | Cuevas et al. |
| 2009/0131917 A1 | 5/2009 | Kavanagh et al. |
| 2009/0137985 A1 | 5/2009 | Tanghoej et al. |
| 2009/0137986 A1 | 5/2009 | Golden et al. |
| 2009/0149837 A1 | 6/2009 | Tanghoj et al. |
| 2009/0156882 A1 | 6/2009 | Chi Sing et al. |
| 2009/0200187 A1 | 8/2009 | Nestenborg et al. |
| 2009/0299334 A1 | 12/2009 | Nishtala et al. |
| 2009/0318900 A1 | 12/2009 | Tanghoj et al. |
| 2010/0198195 A1 | 8/2010 | Nishtala et al. |
| 2010/0228233 A1 | 9/2010 | Kahn |
| 2010/0263327 A1 | 10/2010 | Murray et al. |
| 2010/0324540 A1 | 12/2010 | Paulen et al. |
| 2011/0028943 A1 | 2/2011 | Lawson et al. |
| 2011/0056852 A1 | 3/2011 | Frojd |
| 2011/0114520 A1 | 5/2011 | Matthison-Hansen |
| 2011/0127186 A1 | 6/2011 | Enns et al. |
| 2011/0137296 A1 | 6/2011 | Tanghoj |
| 2011/0184386 A1 | 7/2011 | House |
| 2012/0168324 A1 | 7/2012 | Carleo |
| 2012/0179102 A1 | 7/2012 | Blanchard et al. |
| 2012/0316515 A1 | 12/2012 | Terry |
| 2013/0006226 A1 | 1/2013 | Hong et al. |
| 2013/0048516 A1 | 2/2013 | Nishtala et al. |
| 2013/0153446 A1 | 6/2013 | Utas et al. |
| 2013/0186778 A1 | 7/2013 | Terry |
| 2014/0262859 A1 | 9/2014 | Knapp et al. |
| 2015/0238726 A1 | 8/2015 | Terry |
| 2015/0273116 A1 | 10/2015 | Knapp et al. |
| 2017/0296704 A1 | 10/2017 | Knapp et al. |

FOREIGN PATENT DOCUMENTS

| | | |
|---|---|---|
| CN | 102939127 A | 2/2013 |
| DE | 100 38 521 A1 | 2/2002 |
| DE | 10213411 A1 | 10/2003 |
| EP | 0217771 | 4/1987 |
| EP | 247559 A1 | 12/1987 |
| EP | 0252918 A1 | 1/1988 |
| EP | 0479935 A1 | 4/1992 |
| EP | 0677299 | 10/1995 |
| EP | 0699086 A1 | 3/1996 |
| EP | 0815037 A1 | 1/1998 |
| EP | 0909249 A1 | 4/1999 |
| EP | 0923398 | 6/1999 |
| EP | 0935478 A1 | 8/1999 |
| EP | 0959930 | 12/1999 |
| EP | 0977610 A2 | 2/2000 |
| EP | 1023882 | 8/2000 |
| EP | 1090656 | 4/2001 |
| EP | 1115450 A1 | 7/2001 |
| EP | 1131022 A1 | 9/2001 |
| EP | 1145729 | 10/2001 |
| EP | 1175355 A1 | 1/2002 |
| EP | 1237615 A1 | 9/2002 |
| EP | 1245205 | 10/2002 |
| EP | 1308146 | 5/2003 |
| EP | 1406690 A2 | 4/2004 |
| EP | 1409060 A2 | 4/2004 |
| EP | 1420846 A1 | 5/2004 |
| EP | 1420847 A2 | 5/2004 |
| EP | 1427467 A2 | 6/2004 |
| EP | 1498151 | 1/2005 |
| EP | 1629860 | 3/2006 |
| EP | 1641510 A1 | 4/2006 |
| EP | 1642610 | 4/2006 |
| EP | 1642611 | 4/2006 |
| EP | 2060296 A1 | 5/2009 |
| EP | 2459264 A1 | 6/2012 |
| EP | 2464411 A1 | 6/2012 |
| EP | 2515988 A1 | 10/2012 |
| EP | 2542291 A1 | 1/2013 |
| EP | 3078393 B1 | 11/2017 |
| EP | 2967968 B1 | 9/2018 |
| FR | 2731345 A1 | 9/1996 |
| FR | 2 794 638 A1 | 12/2000 |
| GB | 2284764 | 6/1995 |
| GB | 2319507 | 5/1998 |
| JP | S55-12265 B2 | 3/1980 |
| JP | 2001-500414 A | 1/2001 |
| JP | 2002-530148 A | 9/2002 |
| JP | 2002 282275 A | 10/2002 |
| JP | 2007-501656 A | 2/2007 |
| JP | 2011-510110 A | 3/2011 |
| JP | 2013-500125 | 1/2013 |
| JP | 2013-515572 | 5/2013 |
| RU | 2009105497 A | 8/2010 |
| WO | 198401296 A1 | 4/1984 |
| WO | 1986006284 | 11/1986 |
| WO | 1991005577 A1 | 5/1991 |
| WO | 1994016747 A1 | 8/1994 |
| WO | 1996038192 A1 | 12/1996 |
| WO | 1997026937 | 7/1997 |
| WO | 1997041811 | 11/1997 |
| WO | 1998006642 | 2/1998 |
| WO | 1998011932 | 3/1998 |
| WO | 1998019729 | 5/1998 |
| WO | 98/46176 A1 | 10/1998 |
| WO | 1999030761 A1 | 6/1999 |
| WO | 2000016843 | 3/2000 |
| WO | 2000047494 | 8/2000 |
| WO | 2001043807 | 6/2001 |
| WO | 2001052763 | 7/2001 |
| WO | 2001093935 | 12/2001 |
| WO | 2002036192 | 5/2002 |
| WO | 2003002177 | 1/2003 |
| WO | 2003002178 | 1/2003 |
| WO | 2003008028 | 1/2003 |
| WO | 2003008029 | 1/2003 |
| WO | 2003064279 A1 | 8/2003 |
| WO | 2003092779 | 11/2003 |
| WO | 2004030722 | 4/2004 |
| WO | 2004045696 | 6/2004 |
| WO | 2004045696 A1 | 6/2004 |
| WO | 2004050155 | 6/2004 |
| WO | 2004052440 | 6/2004 |
| WO | 2004056414 | 7/2004 |
| WO | 2004075944 | 9/2004 |
| WO | 2004089454 | 10/2004 |
| WO | 2005004964 | 1/2005 |
| WO | 2005014055 A2 | 2/2005 |
| WO | 2005061035 | 7/2005 |
| WO | 2005092418 | 10/2005 |
| WO | 2007050685 | 5/2007 |
| WO | 2007050685 A2 | 5/2007 |
| WO | 2009012336 A1 | 1/2009 |
| WO | 2007050685 A3 | 4/2009 |
| WO | 2011014201 A1 | 2/2011 |
| WO | 2011019359 A1 | 2/2011 |
| WO | 2011063816 A1 | 6/2011 |
| WO | 2011079129 A1 | 6/2011 |
| WO | 2011109393 A1 | 9/2011 |
| WO | 2014165046 A1 | 10/2014 |

OTHER PUBLICATIONS

AU 2014248744 filed Jul. 9, 2015 Examiner's Report dated Jul. 26, 2017.

BR PI 0506836-3 filed Jan. 18, 2005, Technical Report dated Jul. 28, 2015.

CA 2,769,026 filed Jan. 24, 2012 First Examination Report dated Nov. 4, 2013.

CN 201080058895.4 filed Jun. 21, 2012 First Office Action dated Feb. 27, 2014.

(56) References Cited

OTHER PUBLICATIONS

CN 201080058895.4 filed Jun. 21, 2012 Second Office Action dated Nov. 3, 2014.
CN 201080058895.4 filed Jun. 21, 2012 Third Office Action dated May 4, 2015.
CN 201480013064.3 filed Sep. 8, 2015 Office Action dated Jun. 29, 2017.
CN 201480013064.3 filed Sep. 8, 2015 Office Action dated Oct. 10, 2016.
EP 09848341.5 filed Feb. 27, 2012 extended European Search Report dated Apr. 4, 2013.
EP 09848341.5 filed Feb. 27, 2012 supplemental European Search Report dated Nov. 8, 2013.
EP 10840071.4 filed Jul. 4, 2012 Exam Report dated Apr. 29, 2014.
EP 10840071.4 filed Jul. 4, 2012 extended European Search Report dated Apr. 17, 2013.
EP 10840071.4 filed Jul. 4, 2012 Notice of Opposition dated Apr. 24, 2017.
EP 10840071.4 filed Jul. 4, 2012 Office Action dated Jul. 9, 2015.
EP 11751198.0 filed Sep. 28, 2012 Exam Report dated Feb. 7, 2014.
EP 11751198.0 filed Sep. 28, 2012 extended European search report dated Jul. 9, 2013.
EP 14779919.1 filed Sep. 10, 2015 Extended European Search Report dated Aug. 23, 2016.
EP 14779919.1 filed Sep. 10, 2015 Office Action dated Jul. 4, 2017.
EP 16171279.9 filed May 25, 2016 Extended European Search Report, dated Aug. 23, 2016.
EP 16171279.9 filed May 25, 2016 Intent to Grant, dated Jun. 13, 2017.
JP 2012-546157 filed Jun. 12, 2012 Decision of Rejection dated Aug. 21, 2015.
JP 2012-546157 filed Jun. 12, 2012 First Office Action dated Sep. 16, 2014.
JP 2015-243156 filed Dec. 14, 2015 Office Action dated Sep. 16, 2016.
Norton, J.A. et al., Surgery: Basic Science and Clinical Evidence Springer, 2nd ed., 2008, p. 281.
PCT/US2006/041633 filed Oct. 25, 2006 International Preliminary Report on Patentability dated Mar. 24, 2009.
PCT/US2006/041633 filed Oct. 25, 2006 Search Report dated Aug. 12, 2008.
PCT/US2006/041633 filed Oct. 25, 2006 Written Opinion dated Aug. 12, 2008.
PCT/US2009/055389 filed Aug. 28, 2009 International Search Report dated Oct. 20, 2009.
PCT/US2009/055389 filed Aug. 28, 2009 Written Opinion dated Oct. 20, 2009.
PCT/US2009/055395 filed Aug. 28, 2009 International Preliminary Report on Patentability dated Jan. 31, 2012.
PCT/US2009/055395 filed Aug. 28, 2009 International Search Report dated Oct. 15, 2009.
PCT/US2009/055395 filed Aug. 28, 2009 Written Opinion dated Oct. 15, 2009.
PCT/US2010/061597 filed Dec. 21, 2010 International Preliminary Report on Patentability dated Jun. 26, 2012 and Written Opinion dated Feb. 28, 2011.
PCT/US2010/061597 filed Dec. 21, 2010 International Search Report dated Feb. 28, 2011.
PCT/US2011/026681 filed Mar. 1, 2011 International Preliminary Report on Patentability dated Sep. 4, 2012.
PCT/US2011/026681 filed Mar. 1, 2011 International Search Report dated Apr. 27, 2011.
PCT/US2011/026681 filed Mar. 1, 2011 Written Opinion dated Apr. 27, 2011.
PCT/US2014/024231 filed Mar. 12, 2014 International Search Report and Written Opinion dated Jul. 10, 2014.
U.S. Appl. No. 12/091,916, filed Feb. 2, 2009 Final Office Action dated Sep. 22, 2011.
U.S. Appl. No. 12/091,916, filed Feb. 2, 2009 Non-Final Office Action dated May 10, 2011.
U.S. Appl. No. 12/091,916, filed Feb. 2, 2009 Non-Final Office Action dated Nov. 24, 2010.
U.S. Appl. No. 12/091,916, filed Feb. 2, 2009 Notice of Allowance dated Aug. 17, 2012.
U.S. Appl. No. 13/387,447, filed Mar. 22, 2012 Advisory Action dated Feb. 27, 2014.
U.S. Appl. No. 13/387,447, filed Mar. 22, 2012 Examiner's Answer dated Oct. 5, 2016.
U.S. Appl. No. 13/387,447, filed Mar. 22, 2012 Final Office Action dated Dec. 11, 2013.
U.S. Appl. No. 13/387,447, filed Mar. 22, 2012 Final Office Action dated Oct. 31, 2014.
U.S. Appl. No. 13/387,447, filed Mar. 22, 2012 Final Office Action dated Oct. 5, 2015.
U.S. Appl. No. 13/387,447, filed Mar. 22, 2012 Non-Final Office Action dated Jan. 15, 2013.
U.S. Appl. No. 13/387,447, filed Mar. 22, 2012 Non-Final Office Action dated Jul. 15, 2014.
U.S. Appl. No. 13/387,447, filed Mar. 22, 2012 Non-Final Office Action dated Jun. 6, 2013.
U.S. Appl. No. 13/387,447, filed Mar. 22, 2012 Non-Final Office Action dated Mar. 12, 2015.
U.S. Appl. No. 13/389,753, filed Mar. 20, 2012 Decision on Appeal dated Jun. 29, 2017.
U.S. Appl. No. 13/389,753, filed Mar. 20, 2012 Examiner's Answer dated Aug. 27, 2015.
U.S. Appl. No. 13/389,753, filed Mar. 20, 2012 Final Office Action dated Dec. 10, 2014.
U.S. Appl. No. 13/389,753, filed Mar. 20, 2012 Non-Final Office Action dated Jul. 21, 2014.
U.S. Appl. No. 13/389,753, filed Mar. 20, 2012 Notice of Allowance dated Jul. 5, 2017.
U.S. Appl. No. 13/516,660, filed Aug. 27, 2012 Advisory Action dated Sep. 22, 2016.
U.S. Appl. No. 13/516,660, filed Aug. 27, 2012 Final Office Action dated Jun. 29, 2016.
U.S. Appl. No. 13/516,660, filed Aug. 27, 2012 Non-Final Office Action dated Mar. 8, 2016.
U.S. Appl. No. 13/582,698, filed Sep. 4, 2012 Non-Final Office Action dated Sep. 24, 2014.
U.S. Appl. No. 13/662,278, filed Oct. 26, 2012 Examiner's Answer dated Jun. 2, 2017.
U.S. Appl. No. 13/662,278, filed Oct. 26, 2012 Final Office Action dated Feb. 20, 2015.
U.S. Appl. No. 13/662,278, filed Oct. 26, 2012 Final Office Action dated Oct. 19, 2016.
U.S. Appl. No. 13/662,278, filed Oct. 26, 2012 Non-Final Office Action dated Jul. 7, 2016.
U.S. Appl. No. 13/662,278, filed Oct. 26, 2012 Non-Final Office Action dated Sep. 12, 2014.
U.S. Appl. No. 13/662,278, filed Oct. 26, 2012 Non-Final Office Action dated Sep. 17, 2015.
U.S. Appl. No. 13/802,095, filed Mar. 13, 2013 Non-Final Office Action dated Aug. 15, 2014.
U.S. Appl. No. 13/802,095, filed Mar. 13, 2013 Notice of Allowance dated Nov. 28, 2014.
U.S. Appl. No. 14/681,023, filed Apr. 7, 2015 Non-Final Office Action dated Nov. 9, 2016.
U.S. Appl. No. 14/681,023, filed Apr. 7, 2015 Notice of Allowance dated Mar. 8, 2017.
U.S. Appl. No. 14/707,954, filed May 8, 2015 Non-Final Office Action dated Dec. 1, 2016.
EP 17201044.9 filed Nov. 10, 2017 Extended European Search Report dated Jan. 18, 2018.
JP 2016-501444 filed Sep. 11, 2015 Office Action dated Dec. 14, 2017.
MX/a/2015/009904 filed Jul. 30, 2015 Office Action dated Jun. 29, 2018.
RU 2015140616 filed Sep. 24, 2015 Office Action dated Feb. 21, 2018.
U.S. Appl. No. 13/387,447, filed Mar. 22, 2012 Notice of Allowance dated Jul. 30, 2018.

(56) References Cited

OTHER PUBLICATIONS

U.S. Appl. No. 13/387,447, filed Mar. 22, 2012 Patent Board Decision dated Jun. 1, 2018.
U.S. Appl. No. 13/516,660, filed Aug. 27, 2012 Examiner's Answre dated Nov. 22, 2017.
U.S. Appl. No. 13/662,278, filed Oct. 26, 2012 Board Decision dated Aug. 23, 2018.
Piyush Gupta et al. Hydrogels: from controlled release to pH-responsive drug delivery, May 2002, DDT vol. 7, No. 10, pp. 569-579. (Year 2002).
U.S. Appl. No. 13/516,660, filed Aug. 27, 2012 Board Decision dated Jan. 22, 2019.
U.S. Appl. No. 13/516,660, filed Aug. 27, 2012 Non-Final Office Action dated Mar. 15, 2019.

\* cited by examiner

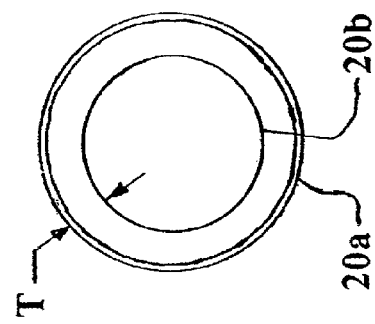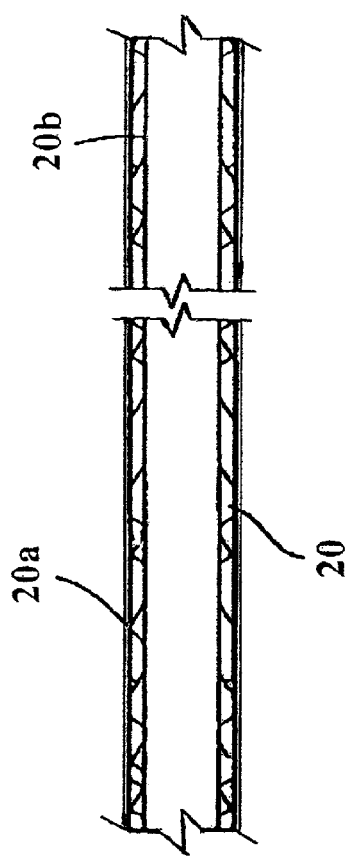

CATHETER ASSEMBLY/PACKAGE UTILIZING A HYDRATING/HYDROGEL SLEEVE AND A FOIL OUTER LAYER AND METHOD OF MAKING AND USING THE SAME

PRIORITY

This application is a continuation of U.S. patent application Ser. No. 14/707,954, filed May 8, 2015, now U.S. Pat. No. 9,731,093, which is a continuation of U.S. patent application Ser. No. 13/582,698, filed Sep. 4, 2012, now U.S. Pat. No. 9,033,149, which is a U.S. national stage application under 35 U.S.C. § 371 of International Application No. PCT/US2011/026681, filed Mar. 1, 2011, which claims priority to U.S. Provisional Patent Application No. 61/310,535, filed Mar. 4, 2010, each of which is incorporated by reference into this application as if fully set forth herein.

BACKGROUND OF THE INVENTION

Intermittent catheterization is a sterile process of draining urine from the bladder when normal draining is impossible or difficult. Proper intermittent catheter use reduces the risk of urinary tract infections and kidney damage. Intermittent catheters come in many different sizes and lengths to fit the body. Some catheters are also available pre-lubricated. Of these, some catheters require their coating be hydrated before insertion. Other catheters have pre-hydrated lubricious coatings for immediate insertion upon opening the package.

Intermittent catheterization is generally performed a minimum of four times a day by the patient or a care giver. The genital area near the urethral opening is wiped with an antiseptic agent, such as iodine. A lubricant may then be used to facilitate the entry of the catheter into the urethra. A topical local anesthetic may also be applied to numb the urethral opening during the procedure. One end of the catheter is placed in a container, and the other end is inserted into and guided up the urethra and into the bladder until urine flow begins.

When urine flow stops, the catheter may be re-positioned, moved or rotated. The patient may also be made to change positions to ensure that all urine has emptied from the bladder. The catheter may then be withdrawn and cleaned for the next use. Recommended cleaning practices vary, from the use of soap and water, to submersion in boiling water or a disinfectant solution. Some patients prefer to use a new catheter with each insertion or catheterization. This is because improper cleaning of re-used catheters can contribute to the development of urinary tract infections (UTI). Patients with recurrent UTIs are encouraged to only use a new catheter for each catheterization.

Intermittent catheters are generally catheters or tubes having a rounded, atraumatic distal tip that is inserted into the bladder of a patient. A molded funnel is typically connected to a distal end that remains outside the body of the patient or user. The distal tip may include slots or openings on the shaft to facilitate drainage of urine therefrom once the tip is positioned inside the bladder.

Hydrophilic-coated intermittent catheters are intermittent catheters having a highly lubricious coating on an outer surface thereof, which are either packaged with fluid or otherwise brought into contact with fluid in order to provide a catheter with a slippery outer surface to facilitate insertion into the patient or user.

Existing hydrophilic-coated intermittent catheters fall into three broad categories. In a first type, the catheter is packaged in a dry environment, but it contains a hydrophilic coating that requires a wetting fluid in order to become hydrated and lubricious. The wetting fluid is obtained from an external source by the user (e.g., sink, bottled water, etc.), and the catheter is positioned within the wetting fluid for a period of time to become hydrated. Use of this first type of intermittent catheter may prove difficult where no clean water or wetting fluid is readily available. Moreover, catheter sterility may be compromised due to the user's handling of the catheter when wetting fluid is applied.

A second type of hydrophilic-coated intermittent catheter is also packaged in a dry environment and contains a lubricious coating. However, the wetting fluid is positioned in a pouch or container within the catheter package itself. To hydrate the catheter, the pouch or container is opened when the user is ready for insertion. Suitable examples of such catheters are disclosed in U.S. Pat. Nos. 7,087,048 and 6,634,498 (the disclosures of which are incorporated herein by reference in their entireties). As with the first type, this second type may be disadvantageous because the catheter must be exposed to the wetting fluid for a period of time before insertion to ensure hydration of the lubricious coating. The sterility of the catheter can also be compromised during insertion. This concern, however, is no different than a pre-wetted catheter because package remains sealed during hydration.

A third type of pre-wetted intermittent catheter is packaged in a wet environment. That is, the catheter is exposed to a wetting fluid within the catheter package, thus hydrating the coating. Suitable examples of such catheters are disclosed in U.S. Pat. Nos. 7,380,658, 6,848,574 and 6,059,107 (the disclosures of which are incorporated herein by reference in their entireties). However, the user may have difficulty handling the catheter due to its slippery surface, and excessive or imprecise handling may result in contamination of the catheter by the user. This could then expose the user to a urinary tract infection.

An example of the third type is shown in FIGS. 1 and 2 of the instant application. As can be seen in these drawings, the catheter assembly utilizes a catheter 1 arranged in a package 2 made of two sheets 2a and 2b which can be separated from each other (see FIG. 2) so as to allow access to the catheter 1. The catheter 1 is arranged in a space 3 arranged within the package 2 along with a hydrating fluid. In this way, the coating C arranged on a tube portion 4 of the catheter 1 is maintained in a hydrated or pre-wetted state. The catheter 1 includes a funnel 7 arranged on a proximal end 8 and a closed and rounded end or tip at a distal end 9. One or more drainage eyelets 5 are arranged in an area of the distal end 9. When user desires to use the catheter assembly shown in FIG. 1, the user need only open the package 2 (see FIG. 2), remove the catheter 1 from the package 2 which is already pre-wetted, and insert the distal end 9 into the bladder.

Existing intermittent catheters may also drain urine into a bag. Following bladder drainage into the bag, the bag may be emptied by inverting and tearing a notch. Urine is then drained into a receptacle through the tear. That process can be slow, messy, and subject to urine spills.

Non-intermittent catheterization, which is used in a hospital or nursing home setting, uses the same basic technique for insertion of the urinary tract catheter. The catheter is inserted by a nurse or other health care professional, and, it remains in the patient until bladder function can be maintained independently. When the catheter is removed, patients experience a pulling sensation and may feel some minor discomfort. If the catheter is required for an extended period of time, a long-term, indwelling catheter, such as a Foley catheter, is used. To prevent infection, it should be regularly exchanged for a new catheter every three to six weeks.

Proper catheter use can also often be determined by the length of time that the process is necessary: long-term (often called indwelling) or short-term use. In some situations, incontinent patients are catheterized to reduce their cost of care. A condom catheter, which fits on the outside of the penis using adhesive, can be used for short-term catheterization in males. However, long-term catheterization is not recommended because chronic use carries a significant risk of urinary tract infection. This risk catheterization should only be considered as a last resort for the management of incontinence where other measures have proved unsuccessful and where there is significant risk to the skin.

A catheter that is left in place for a period of time may be attached to a drainage bag to collect the urine. There are two types of drainage bags. One is a leg bag being a smaller drainage device that attaches by elastic bands to the leg. A leg bag is usually worn during the day, as it fits discreetly under pants or skirts, and is easily emptied into a toilet. The second type of drainage bag is a larger device called a down drain that may be used during the night. This device is usually hung on the patient's bed or placed on the floor nearby.

During long-term use, the catheter may be left in place the entire duration, or a patient may be instructed on an intermittent self-catheterization procedure for placing a catheter just long enough to empty the bladder and then removing it. Patients undergoing major surgery are often catheterized and may remain so for long durations. Long-term catheterization can expose patients to an increased risk of infection. Long-term catheterization as a remedy for incontinence is not appropriate, as the risks outweigh the benefits.

In males, for example, the catheter tube is inserted into the urinary tract through the penis. Insertion in males can sometimes be difficult because of the abrupt angle in the male's urethra. An external device such as a condom catheter can also be used. In females, the catheter is inserted into the urethral meatus, after a cleansing. The procedure can be complicated in females due to varying layouts of the genitalia (due to age, obesity, childbirth, or other factors), but a good clinician should rely on anatomical landmarks and patience when dealing with such patients.

Common indications to catheterize a patient include acute or chronic urinary retention (which can damage the kidneys), orthopedic procedures that may limit a patient's movement, the need for accurate monitoring of input and output (such as in an ICU), benign prostatic hyperplasia, incontinence, and the effects of various surgical interventions involving the bladder and prostate.

For some patients the insertion and removal of a catheter can cause excruciating pain, so a topical anesthetic can be used for patients of both sexes. Catheterization should be performed as a sterile medical procedure and should only be done by trained, qualified personnel, using equipment designed for this purpose. However, in the case of intermittent self catheterization, the patient can perform the procedure his/her self. If correct technique is not used, trauma may be caused to the urethra or prostate (male). A urinary tract infection or paraphimosis may also occur (male uncircumcised patient).

Particular complications of catheter use may include: urinary tract or kidney infections, blood infections (sepsis), urethral injury, skin breakdown, bladder stones, and blood in the urine (hematuria). After many years of catheter use, bladder cancer may also develop. In using indwelling (long-term) catheters, it is particularly very important to take everyday care of the catheter and the drainage bag.

Catheters come in a large variety of sizes, materials (latex, silicone, PVC, or Teflon-coated), and types (Foley catheter, straight catheter, or coude tip catheter). In the case of internal catheters, those inserted into the urethra, the smallest size is usually recommended, although a larger size is sometimes needed to control leakage of urine around the catheter. A large size can also become necessary when the urine is thick, bloody or contains large amounts of sediment. Larger internal catheters, however, are more likely to cause damage to the urethra. Some people develop allergies or sensitivities to latex after long-term latex catheter use or prior latex exposure. In such cases, catheters made of materials other than natural rubber latex should be used. Silver coated urinary catheters may also be used to reduce infections.

Catheter diameters are sized by the French catheter scale (F). The most common sizes are 10 F to 28 F. The clinician selects a size large enough to allow free flow of urine, but large enough to control leakage of urine around the catheter. A larger size can become necessary when the urine is thick, bloody or contains large amounts of sediment. Larger catheters, however, are more likely to cause damage to the urethra. (Jeffrey A N et al., Surgery: Basic Science and Clinical Evidence Springer, 2nd ed., 2008, p. 281).

Catheters are regulated as class II medical devices under section 513 of the Federal Food, Drug, and Cosmetic Act (the act) and the appropriate panel (78 Gastroenterology/Urology) as described in 21 CFR 807.87(c).

Finally, it is noted that existing intermittent catheters typically have two staggered drainage eyelets or openings which are located on a distal end of the catheter, i.e., near the inserting tip. These openings allow the catheter to drain urine from the bladder.

SUMMARY OF THE INVENTION

The present invention is directed to easy-to-use urinary catheter assemblies that eliminate or minimize some of the shortcomings of prior art devices. The catheter can be a single-use catheter and/or may be packaged as a single-use device. Non-limiting embodiments of the invention include one or more features described herein and/or shown in the drawings in combination with one of more prior art features discussed above.

Non-limiting embodiments of the invention provide for an improved pre-wetted catheter which maintain a coating of the catheter tube in a hydrated state using a hydrating sleeve and a foil outer layer or package.

Non-limiting embodiments of the invention also provide for improved pre-wetted catheter whose package can be opened without any significant spilling of moisture or fluid from the package.

Non-limiting embodiments of the invention also provide for improved pre-wetted catheter having a sleeve which contains all or substantially all of the hydrating fluid and that is packaged and/or arranged in a foil member.

Non-limiting embodiments of the invention also provide for a catheter assembly comprising an elongate member having a proximal end and a distal end. The distal end has at least one drainage opening. A fluid containing member is arranged on the elongate member. A foil container contains the elongate member and the fluid containing member.

Non-limiting embodiments of the invention also provide for a method of inserting the catheter assembly of any one of the types described above, wherein the method comprises removing the elongate member from the fluid containing member and inserting the elongate member into a user's body. The method may further comprise draining fluid or urine from the user's body.

Non-limiting embodiments of the invention also provide for a catheter assembly comprising an elongate member having a proximal end and a distal end. The distal end has at least one drainage opening. A fluid containing member is arranged on the elongate member or in close proximity to provide a means of maintaining the hydrophilic coating in its hydrated and lubricious state or to provide a fluid reservoir for hydration of the coating inside a package before the package is opened. In embodiments, the fluid containing member is arranged on the elongate member when in the package. In other embodiments, the fluid containing member is not arranged on the elongate member when in the package.

The invention comprises at least one of; a foil container containing the elongate member and the fluid containing member, a container having a foil layer and containing the elongate member and the fluid containing member, a foil layer surrounding a substantial portion of the fluid containing member, a package having at least one foil layer and containing therein at least the fluid containing member, a sealed package having at least one foil layer and containing therein the fluid containing member and the elongate member, a fluid impermeable package having at least one foil layer and containing therein the fluid containing member and the elongate member, a foil layer surrounding substantially all of the fluid containing member, at least one foil layer secured to an outer surface of the fluid containing member, a generally cylindrical foil layer containing therein a substantially portion of the fluid containing member, and a generally cylindrical foil layer containing therein substantially all of the fluid containing member.

The fluid containing member may be a hydrogel sleeve. The fluid containing member may have a wall thickness that is ⅛ inch or greater. The fluid containing member may be generally cylindrical. The fluid containing member may be structured and arranged to maintain a coating of the elongate member is a hydrated condition. The fluid containing member may be a tube having an inside diameter sized to receive therein the elongate member. The fluid containing member may comprise an extruded polyurethane tube. The fluid containing member may comprise a polyurethane hydrogel type material. A non-limiting example includes D6/40 (AdvanSource Biomaterials) which is a polyether polyurethane-urea. The fluid containing member may also comprise a hydrophilic polymer.

By way of non-limiting examples, the hydrophilic polymer of the fluid containing member may comprise at least one of; polyethylene oxide, polyethylene glycol, polypropylene glycol, poly vinyl alcohol, carboxy methyl cellulose, hydroxyethyl cellulose, hydroxyl ethyl methacrylate, polyacrylic acid, polyacrylamide, and collagen. The fluid containing member may comprise a material which swells when exposed to a fluid and which absorbs and retains fluid in a wall between an inner diameter and an outer diameter. The fluid containing member may be structured and arranged to swell when exposed to a fluid. The fluid containing member may be structured and arranged to swell when exposed to water. The fluid containing member may be structured and arranged to absorb about 90% of its weight in fluid. The fluid containing member may be structured and arranged to absorb about 90% of its weight in water. The fluid containing member comprises a hydrated polyurethane tube.

The container may be a fluid impermeable package and substantially or nearly all fluid contained in the container is disposed in the fluid containing member. The elongate member may comprise one of; a hydrateable coating arranged at least on an outer surface of the distal end thereof, a lubricious coating arranged at least on an outer surface of the distal end thereof, and a hydrophilic biocompatible coating arranged at least on an outer surface of the distal end.

The catheter assembly is an intermittent catheter assembly. The fluid containing member may be the only device containing fluid in the container. The fluid containing member may be non-removably coupled to the container. The elongate member may be removable from the container without fluid leaking out of the container. The elongate member may be removable from the container while the fluid containing member is retained within the container. The elongate member may comprise a proximal end which is not wetted and/or covered by the fluid containing member. The elongate member may be removable from the container with the fluid containing member. The fluid containing member may comprise a gripping end which does not contain fluid and/or which allows a user to grip the fluid containing member without the user's fingers becoming wetted by fluid.

The container may comprise a first compartment containing the elongate member and a second compartment containing the fluid containing member. The elongate member may be removable from the first compartment and insertable into the second compartment. The elongate member may be removable from the first compartment and insertable into the fluid containing member of the second compartment. A first removable cover may allow the user to access and remove the elongate member from the first compartment and a second removable cover allowing the user to insert the elongate member into the second compartment. The first compartment and the second compartment may comprise separate fluid impermeable compartments.

The container may comprise a foil outer member which substantially encloses the elongate member and completely encloses the fluid containing member. The fluid containing member may be non-removably coupled to the foil outer member. The fluid containing member may be non-removably coupled to an inside diameter of the foil outer member. The foil outer member may comprise a first portion that surrounds a proximal portion of the elongate member and a second portion that surrounds the fluid containing member. The foil outer member may comprise a first portion that surrounds a funnel portion of the elongate member and a second portion that surrounds the fluid containing member and a coated tube portion of the elongate member. The foil outer member may have a length that is substantially equal to a length of the elongate member and the fluid containing member has a length that is substantially equal to the coated tube portion of the elongate member.

The container may comprise an outer tubular member having at least one foil inner layer which completely encloses the elongate member and completely encloses the fluid containing member. The fluid containing member may be arranged within another container arranged within the outer tubular member. The other container containing the fluid containing member may be removable from the outer tubular member. The other container containing the fluid containing member may be non-removable from the outer tubular member. The outer tubular member may comprise a removable cover.

The container may enclose the elongate member and the fluid containing member while axially separated from each other. The container may contain a single compartment which encloses the elongate member and the fluid containing member while axially separated from each other. The container may comprise a single flexible compartment which encloses the elongate member and the fluid containing member while axially separated from each other and is configured to allow the user to position the elongate member into the fluid containing member while the elongate member and the fluid containing member remain enclosed within the single flexible compartment.

The invention also provides for a method of inserting the catheter assembly of any one of the types described herein, wherein the method comprises removing the elongate member from the fluid containing member and inserting the elongate member into a user's body. The method may further comprise draining fluid or urine from the user's body.

The invention also provides for a catheter assembly comprising a catheter having a proximal end, a distal end, and a tubular portion arranged therebetween. The distal end has at least one drainage opening. A fluid containing sleeve is arranged on the tubular portion and maintains a coating of the tubular portion in a hydrated state. A container has at least one foil inner layer and contains therein the catheter and the fluid containing sleeve. Substantially or nearly all fluid contained in the container is disposed in the fluid containing sleeve.

At least one of; the fluid containing sleeve may be a hydrogel sleeve, the fluid containing sleeve may have a wall thickness that is ⅛ inch or greater, the fluid containing sleeve may comprise an extruded polyurethane tube, the fluid containing sleeve may comprise D6/40 polyurethane, the fluid containing sleeve may comprise a hydrophilic polymer and the hydrophilic polymer may comprise at least one of; polyethylene oxide, poly vinyl alcohol, carboxy methyl cellulose, hydroxyl ethyl methacrylate, acrylic polymers, and callagen.

The fluid containing sleeve may comprise a material which swells when exposed to a fluid and which absorbs and retains fluid in a wall between an inner diameter and an outer diameter. The fluid containing sleeve may be structured and arranged to swell when exposed to a fluid. The fluid containing sleeve may be structured and arranged to swell when exposed to water. The fluid containing sleeve may be structured and arranged to absorb about 90% of its weight in fluid. The fluid containing member may be structured and arranged to absorb about 90% of its weight in water. The fluid containing member may comprise a hydrated polyurethane tube.

The invention also provides for a catheter assembly comprising a catheter having a funnel, a tubular portion and at least one drainage opening and a fluid containing sleeve structured and arranged to swell when exposed to a fluid. The fluid containing sleeve is arranged on the tubular portion and maintains a coating of the tubular portion in a hydrated state. An outer sleeve has at least one foil inner layer arranged to surround substantially all of the fluid containing sleeve. A container contains therein the catheter, the fluid containing sleeve, and the outer sleeve. Substantially or nearly all fluid contained in the container is disposed in the fluid containing sleeve.

The invention also provides for a catheter assembly comprising a catheter having a funnel, a tubular portion and at least one drainage opening and a fluid containing sleeve structured and arranged to swell when exposed to a fluid. The fluid containing sleeve is arranged on the tubular portion and maintains a coating of the tubular portion in a hydrated state. An outer sleeve has at least one foil layer arranged to surround substantially all of the fluid containing sleeve. A fluid impermeable container contains therein the catheter, the fluid containing sleeve, and the outer sleeve. Substantially or nearly all fluid contained in the container is disposed in the fluid containing sleeve.

The invention also provides for a catheter assembly comprising a catheter having a funnel, a tubular portion and at least one drainage opening and a fluid containing sleeve structured and arranged to swell when exposed to a fluid. The fluid containing sleeve is sized and configured to slide onto and off of the tubular portion and, when slid on, to maintain a coating of the tubular portion in a hydrated state. At least one foil layer is arranged to surround substantially all of the fluid containing sleeve. A container contains therein the catheter, the fluid containing sleeve, and the outer sleeve. Substantially or nearly all fluid contained in the container is disposed in the fluid containing sleeve.

The invention also provides for a catheter assembly comprising a catheter having a funnel, a tubular portion and at least one drainage opening and a fluid containing sleeve structured and arranged to swell when exposed to a fluid. The fluid containing sleeve is sized and configured to slide onto and off of the tubular portion and, when slid on, to maintain a coating of the tubular portion in a hydrated state. A container contains therein the catheter and the fluid containing sleeve. At least one foil layer is arranged between an inner surface of the container and an outer surface of the fluid containing sleeve. Substantially or nearly all fluid contained in the container is disposed in the fluid containing sleeve.

The invention also provides for a catheter assembly comprising a catheter having a funnel, a tubular portion and at least one drainage opening and a fluid containing sleeve structured and arranged to swell when exposed to a fluid. The fluid containing sleeve is sized and configured to slide onto and off of the tubular portion and, when slid on, to maintain a coating of the tubular portion in a hydrated state. A container contains therein the catheter and the fluid containing sleeve and comprises at least one foil inner layer. Substantially or nearly all fluid contained in the container is disposed in the fluid containing sleeve.

The container may comprise a first compartment containing the catheter and a second compartment containing the fluid containing sleeve.

BRIEF DESCRIPTION OF DRAWINGS OF THE EXEMPLARY EMBODIMENTS

FIG. 4 shows a side cross-sectional view of the catheter and hydrating sleeve used in the assembly package of FIG. 3.

FIG. 5 shows a side cross-sectional view of the hydrating sleeve used in the assembly package of FIG. 3.

DETAILED DESCRIPTION OF THE EXEMPLARY EMBODIMENTS

The following description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will enable one skilled in the art to make and use the invention, and describes several embodiments, adaptations, variations, alternatives and uses of the invention, including what is presently believed to be the best mode of carrying out the invention.

As used herein, the reference terms "proximal" and "distal" (proximal being closer than distal) refer to proximity with respect to a health care professional catheterizing a patient. For example, the region or section of the catheter apparatus that is closest to the health care professional during catheterization is referred to herein as "proximal," while a region or section of the catheter apparatus closest to the patient's bladder is referred to as "distal." In the case of a self-catheterizing patient, proximal refers to a point external to the patient's body, and distal refers to a point within the patient's body (i.e., the bladder).

The catheter assemblies as described herein are discussed in the context of a urinary catheter for insertion into a bladder for drainage of urine therefrom. The instant catheter assemblies, however, may also be used for other applications not specifically mentioned herein. As such, the instant invention is not limited to urinary catheter applications.

Figure 3:
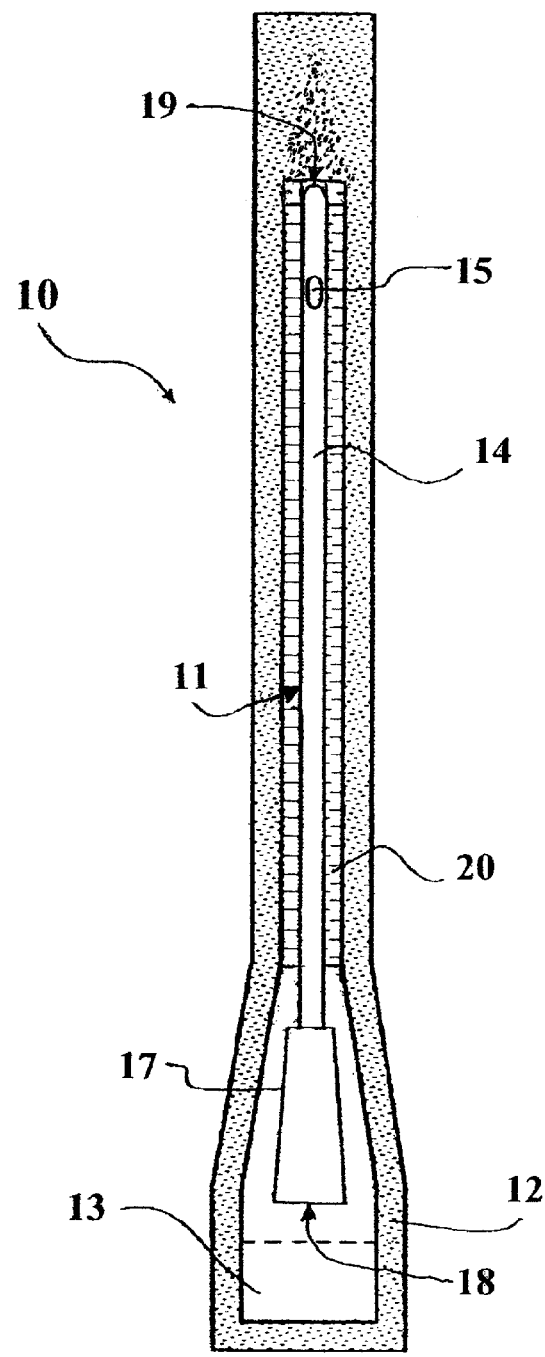
FIG. 3 shows a pre-wetted catheter assembly package in accordance with one non-limiting embodiment of the invention.

FIG. 3 shows a non-limiting embodiment of a pre-wetted urinary catheter assembly package of the present invention. FIG. 3 shows the catheter assembly package in a storage position and/or prior to use configuration.

Figure 1:
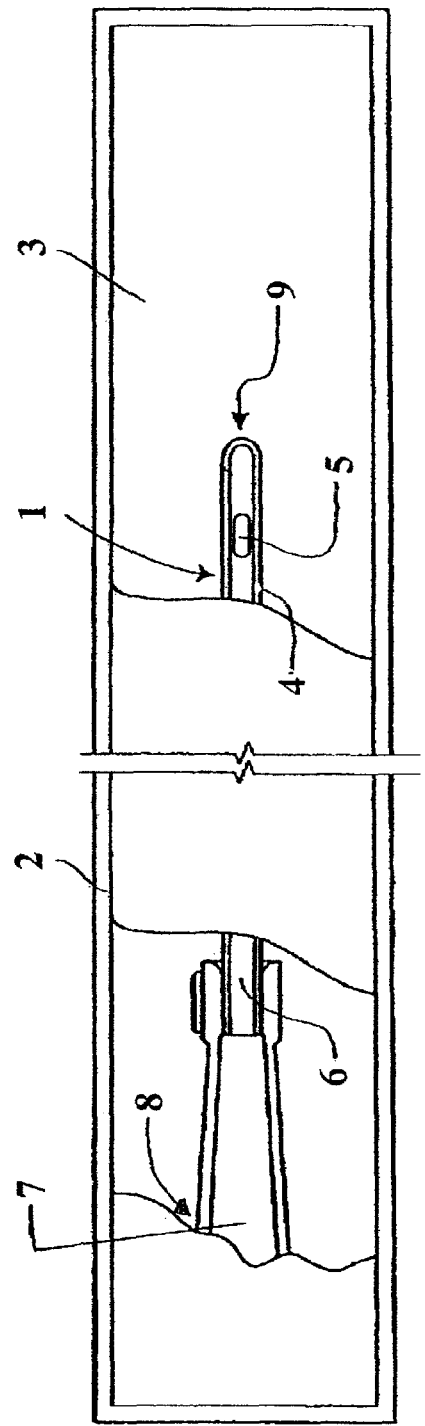
FIG. 1 shows a pre-wetted catheter assembly package in accordance with the prior art.
Figure 2:
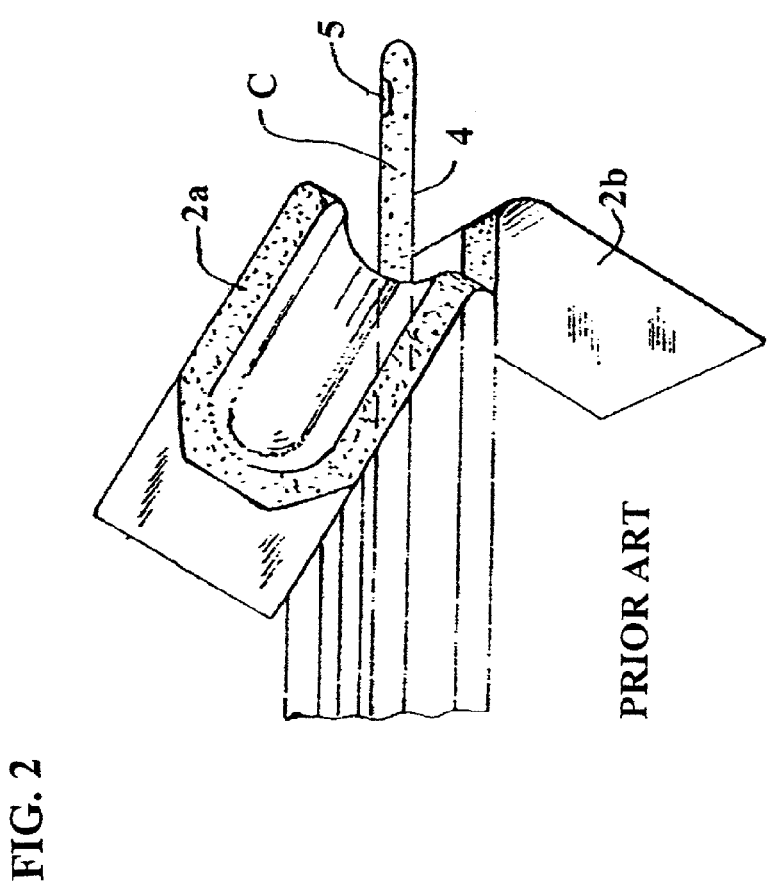
FIG. 2 shows the catheter assembly of FIG. 1 being opened for use by separating two portions which form the package.

The assembly package 10 shown in FIG. 3 includes a catheter 11 arranged within a container 12 which can be in the form of a generally flexible material package such as the type shown in FIG. 2. The catheter assembly 11 includes a catheter having an insertable elongate tube portion 14, one or more drainage eyelets 15, a funnel 17, a proximal end 18, and a distal end 19. A fluid containing sleeve 20 is arranged in the package 12 and is positioned over a substantial portion of the tube 14. The sleeve 20 contains all or nearly all of the fluid that is arranged in the container 12 and is in direct contact with a coating of the tube 14. In embodiments, the funnel 17 remains in a dry state in a non-fluid containing space 13 of the package 12. Thus, only the portion of the catheter in contact with the sleeve 20, i.e., all, nearly all, or most of the tube 14, is wetted or maintained in a pre-wetted state. In embodiments, the sleeve 20 is non-removably connected to the package 12 so that when the user tears (e.g., along the dashed-line in space 13) or splits open the end of the package 12 defining space 13, the user can grip the funnel 17 and slide the catheter out of the package 12 and the sleeve 20 (which remains in the package 12). Since all or nearly all of the fluid which hydrates the coating of the tube 14 is disposed in the sleeve 20, removing the catheter will not cause any fluid to spill out of the package 12 when opened. Furthermore, if the sleeve 20 remains in the package 12, the user need not come into contact with the fluid. Once the catheter is removed from the package 12, it can be inserted into the user's body while the user grips the funnel 17. As is the case with conventional catheters, the coating of the tube 14 is, in embodiments, a lubricious coating to facilitate insertion of the catheter into the user's body.

In embodiments, the package 12 is made of foil material which ensures that the catheter assembly 11 and the sleeve 20 are not dehydrated. The package 12 also ensures that its contents are sealed in a gas and/or fluid tight and/or impermeable manner so that hydrating fluid will not leak out. In embodiments, at least an inner layer, i.e., the layer in contact with the sleeve 20, of the package 12 is made of a foil material. In embodiments, the package 12 is made of a single layer foil material. In embodiments, the package 12 is made of plural layers of different materials with at least one layer being a foil material.

Figure 6:
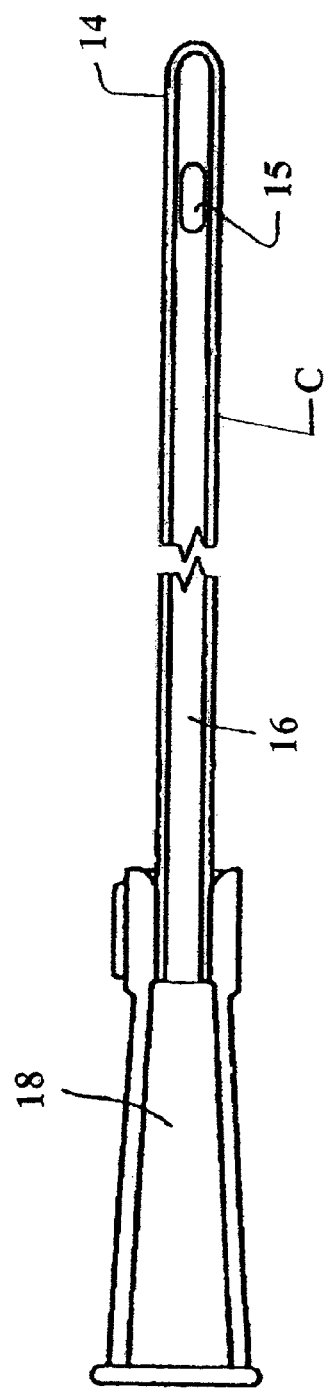
FIG. 6 shows a side cross-sectional view of the catheter used in the assembly package of FIG. 3. In embodiments, the coating can terminate about one inch from the funnel.

In order to form the assembly package of FIG. 3, in embodiments, a catheter of the type shown in, e.g., FIG. 6, can be inserted into a fluid containing sleeve 20 so as to form a sub-assembly. However, prior to insertion into the sleeve 20, the sleeve 20 can be exposed to or immersed in a fluid such as water. Since the sleeve 20 is made of a material that can absorb fluid and expand, this causes the sleeve 20 to swell until it reaches a wall thickness (similar to thickness T in FIG. 5). In this swollen state, the sleeve 20 retains the fluid between an inside diameter and an outside diameter. Once the sleeve 20 is slid onto the catheter, it can maintain the coating of the tube 14 is a hydrated state. This sub-assembly can then be slid into the package 12. Furthermore, since the package 12 is fluid impermeable, it ensures that the fluid in the sleeve 20 cannot escape the package 12 or be contaminated with outside the package 12. In embodiments, the inside diameter of the sleeve 20 is fluid permeable and wets and hydrates the coating of the tube 14 when contacting the tube 14. In embodiments, the outside diameter of the sleeve 20 is also fluid permeable and slightly wets the package 12 when contacting the same. However, unlike the coating of the tube 14, the package 12 does not absorb the fluid. In embodiments, the outside diameter of the sleeve 20 can alternatively be made fluid impermeable so as not to wet the package 12 when contacting the same.

In order to form the assembly package of FIG. 3, in other embodiments, a catheter, e.g., of the type shown in FIG. 6, can be inserted into a fluid containing sleeve 20 after the sleeve 20 is already installed in the package 12. However, prior to insertion into the package 12, the sleeve 20 can be exposed to or immersed in a fluid such as water. Since the sleeve 20 is made of a material that can absorb fluid and expand, this causes the sleeve 20 to swell until it reaches a full or nearly fill fluid swollen wall thickness. In this swollen state, the sleeve 20 retains the fluid between an inside diameter and an outside diameter. Once the catheter is slid into the sleeve 20 already disposed in the package 12, it can maintain the coating of the tube 14 is a hydrated state.

In order to form the assembly package of FIG. 3, in still other embodiments, a catheter, e.g., of the type shown in FIG. 6, can be inserted into a fluid containing sleeve 20 after the sleeve 20 is already installed in the package 12. After insertion into the package 12, the sleeve 20 and package 12 can be exposed to or immersed in a fluid such as water. Since the sleeve 20 is made of a material that can absorb fluid and expand (even while the package 12 cannot absorb fluid), this causes the sleeve 20 to swell until it reaches a swollen wall thickness. In this swollen state, the sleeve 20 retains the fluid between an inside diameter and an outside diameter. Once the catheter is slid into the sleeve 20 disposed in the package 12, the package 12 is sealed closed. The sleeve 20 can then maintain the coating of the tube 14 in a hydrated state while both are inside the package 12.

In still other embodiments, in order to form the assembly package of FIG. 3, a catheter, e.g., of the type shown in FIG. 6, can be inserted into the package 12 after an inner surface of the package 12 is coated with a fluid containing material which, due to the shape of the package 12, can produce a sleeve 20. After or before insertion of the catheter into the package 12, at least the sleeve 20 can be exposed to or immersed in a fluid such as water. Since the sleeve 20 is made of a material that can absorb fluid and expand, this causes the sleeve 20 to swell until it reaches a swollen wall thickness. In this swollen state, the sleeve 20 retains the fluid between an inside diameter and an outside diameter. Once the catheter is slid into the sleeve 20 disposed in the package 12, the package 12 is sealed closed. The sleeve 20 can then maintain the coating of the tube 14 in a hydrated state while both are inside the package 12.

In still other embodiments, the material forming the sleeve 20 can be applied to and/or coated onto the material forming the package 12 so as to form a package having a fluid absorbing and storing inner liner material. In other embodiments, the material forming the sleeve 20 can be co-extruded with the material forming the package 12 so as to form a package having a fluid absorbing and storing inner liner material. In other embodiments, the material forming the sleeve 20 is laminated with the material forming the package 12 so as to form a package having a fluid absorbing and storing inner liner material.

The elongate member 14 can have any size and shape typically utilized in conventional catheters such as generally cylindrical and defines an interior lumen or space which allows fluid to pass and/or drain through. The proximal end 18 includes a funnel which can be of any type that is typically utilized in catheters. The funnel can be connected to any type fluid collection system or bag that is typically utilized in catheters. By way of non-limiting example, the funnel can be a rubber or plastic drainage funnel disposed and friction-fitted on the proximal end of the member 14. A disposable bag (not shown) may be disposed on and/or coupled to the drainage funnel to collect the patient's urine. The distal end 19 of member 14 also includes a tip. The tip is arranged on a forward most portion of the distal end and defines the insertion end of the catheter. The elongate member 14 also preferably contains a biocompatible, hydrophilic, or lubricious coating on its outer surface which is hydrated by the sleeve 20. The coating may also have antimicrobial properties or contain an antimicrobial agent.

FIGS. 4 and 5 show a non-limiting embodiment of a catheter coating hydrating sleeve 20. The sleeve 20 is made of a material that can absorb fluid and expand, this causes the sleeve 20 to swell until it reaches a wall thickness T (see FIG. 5). In this swollen state, the sleeve 20 retains the fluid between an inside diameter 20b and an outside diameter 20a. In embodiments, the sleeve 20 includes an outer generally cylindrically shaped foil layer whose outside diameter defines an outside diameter 20a of the sleeve 20 and an inner generally cylindrical layer of fluid absorbing material which defines an inside diameter 20b of the sleeve 20.

According to another non-limiting embodiment, the hydrating sleeve 20 shown in FIGS. 4 and 5 can be utilized in the type of package 12 shown in FIG. 3.

Figure 7:
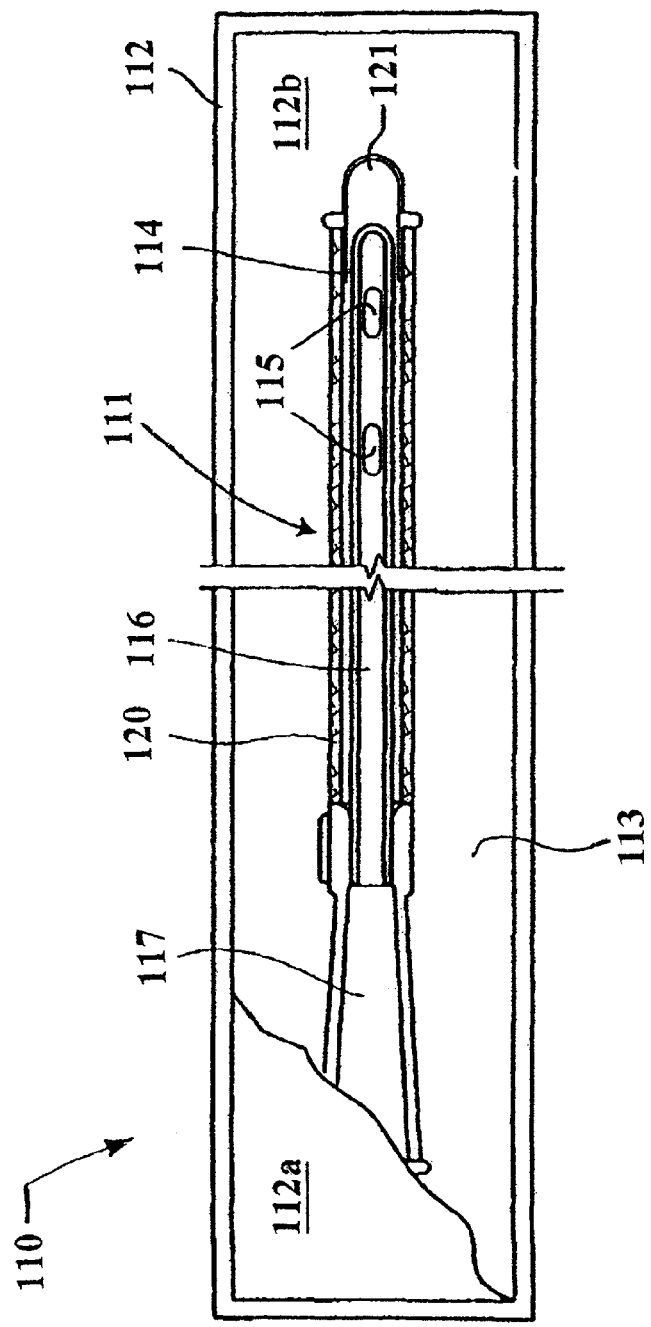
FIG. 7 shows a pre-wetted catheter assembly package in accordance with another non-limiting embodiment of the invention.

FIG. 7 shows another non-limiting embodiment of a pre-wetted urinary catheter of the present invention. In FIG. 7, the catheter assembly package is in a storage position and/or prior to use configuration.

The assembly package 110 shown in FIG. 7 includes a catheter 111 arranged within a container 112 which can be in the form of a generally flexible material package similar to that shown in FIG. 2, but somewhat larger to allow (or provide space for) the catheter 111 to more freely move therein. In embodiments, the package 112 can be formed of package sheets 112a and 112b which are connected together in peripheral seam areas. The catheter assembly 111 includes a catheter having an insertable elongate tube portion 114, one or more drainage eyelets 115, a funnel 117 arranged on a proximal end, and a distal end. A fluid containing sleeve 120 is arranged in the package 112, and is positioned over a substantial portion of the tube 114. The sleeve 120 utilizes a gripping portion 121 secured to a forward end of the sleeve 120 which allows the user to grip and remove the sleeve 120 from the catheter. As with the previous embodiments, the sleeve 120 contains all or nearly all of the fluid that is arranged in the container 112, and is in direct contact with a coating of the tube 114. The package can be designed such that, in embodiments, the funnel 117 and gripping portion 121 generally remain in a dry or mostly dry state in a non and/or generally low-fluid containing space 113 of the package 112. Thus, only the portion of the catheter in contact with the sleeve 120, i.e., all, nearly all, or most of the tube 114, is wetted or maintained in a pre-wetted state.

In embodiments, the sleeve 120 is removable from the package 112 with the catheter as assembly 111 when the user tears or splits open one end of the package 112. Once removed from the package 112, the user can grip the funnel 117 with one hand and the gripping portion 121 with the other hand, and then slide the catheter out of the sleeve 120 and/or slide the sleeve 120 off of the catheter 111. Since all or nearly all of the fluid which hydrates the coating of the tube 114 is disposed in the sleeve 120, removing the catheter assembly 111 from the package 112 will not cause any (or hardly any) fluid to spill out of the package 112 when opened. Furthermore, if the sleeve 120 is gripped by the end 121 and placed back into the package 112, the user need not come into contact with the fluid. Once the catheter 111 is removed from the package 112, it can be inserted into the user's body while the user grips the funnel 117. As is the case with conventional catheters, the coating of the tube 114 is, in embodiments, a lubricious coating to facilitate insertion of the catheter into the user's body.

In order to form the assembly package of FIG. 7, in embodiments, a catheter, e.g., of the type shown in FIG. 6, can be inserted into the fluid containing sleeve 120 shown in FIG. 7. However, prior to insertion into the sleeve 120, the sleeve 120 can be exposed to or immersed in a fluid such as water. Since the sleeve 120 is made of a material that can absorb fluid and expand, this causes the sleeve 120 to swell until it reaches a wall thickness (similar to thickness T that shown in FIG. 5). In this swollen state, the sleeve 120 retains the fluid between an inside diameter and an outside diameter. Once the sleeve 120 is slid onto the catheter as shown in FIG. 7, it can maintain the coating of the tube 114 is a hydrated state. This sub-assembly of the catheter 111 and sleeve 120 can then be slid into the package 112. Furthermore, since the package 112 is fluid impermeable, it ensures that the fluid in the sleeve 120 cannot escape the package 112 or be contaminated with outside the package 112. In embodiments, the inside diameter of the sleeve 120 is fluid permeable and wets and hydrates the coating of the tube 114 when contacting the tube 114. In embodiments, the outside diameter of the sleeve 120 is also fluid permeable and slightly wets the package 112 when contacting the same. However, unlike the coating of the tube 114, the package 112 does not absorb the fluid. In embodiments, the outside diameter can alternatively be made fluid impermeable so as not to wet the package 112 when contacting the same.

In embodiments, the package 112 is made of foil material which ensures that the catheter assembly 111 and the sleeve 120 are not contaminated. The package 112 also ensures that its contents are sealed in a gas and/or fluid tight and/or impermeable manner so that hydrating fluid will not leak out. In embodiments, at least an inner layer, i.e., the layer in contact with the sleeve 120, of the package 112 is made of a foil material. In embodiments, the package 112 is made of a single layer foil material. In embodiments, the package 112 is made of plural layers of different materials with at least one layer being a foil material.

According to another non-limiting embodiment, the hydrating sleeve 120 shown in FIG. 7 can utilize a sleeve configuration of the type shown in FIGS. 4 and 5, i.e., the sleeve 120 can have a hydration containing inner sleeve layer and a foil outer layer.

Figure 8:
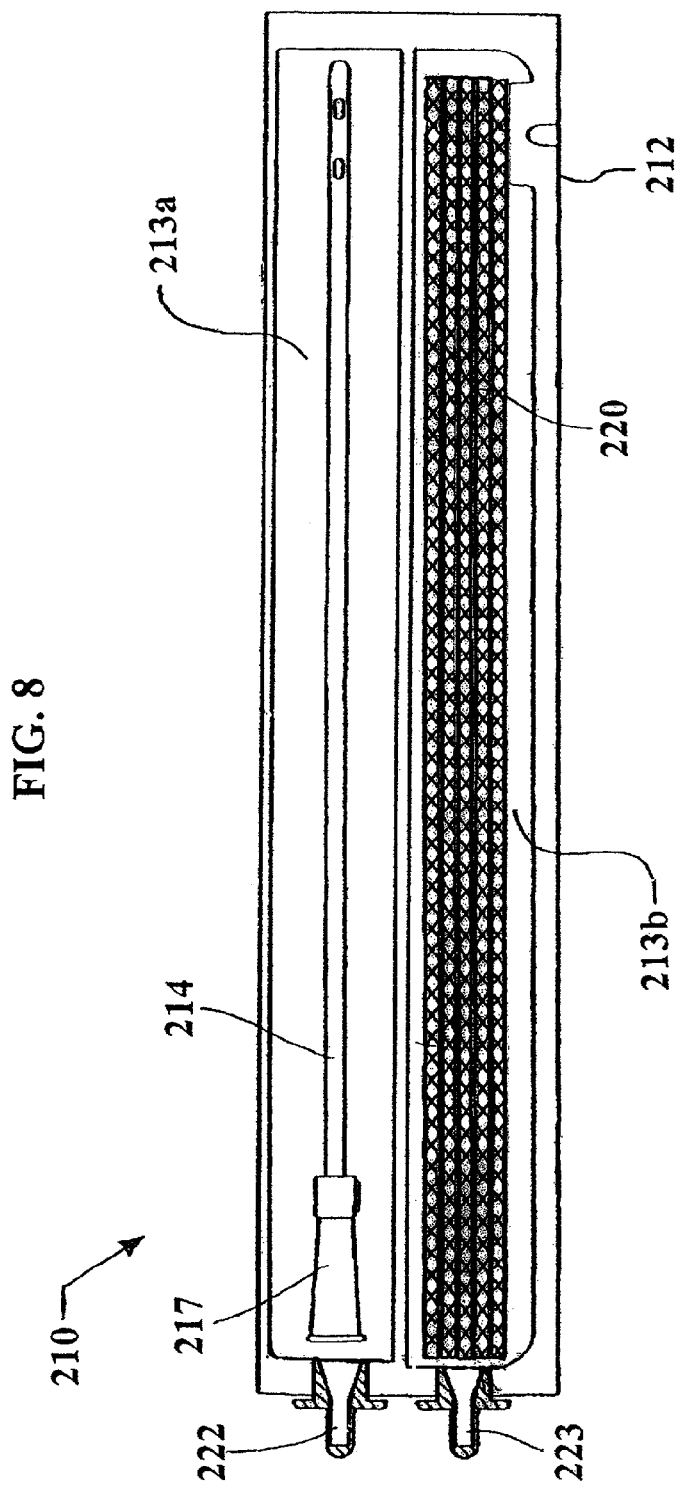
FIG. 8 shows a pre-wetted catheter assembly package in accordance with still another non-limiting embodiment of the invention.

FIG. 8 shows another non-limiting embodiment of a pre-wetted urinary catheter of the present invention. In FIG. 8, the catheter assembly package is in a storage position and/or prior to use configuration.

The assembly package 210 shown in FIG. 8 includes a catheter arranged within a first compartment 213a of a container 212 which can be in the form of a generally flexible package similar to the type shown in FIG. 2. A fluid containing sleeve 220 is arranged within a second compartment 213b of the container 212. The catheter has an insertable elongate tube portion 214, one or more drainage eyelets, a funnel 217 arranged on a proximal end, and a distal end. The fluid containing sleeve 220 is sized to be positioned over and onto a substantial portion of the tube 214. When the user desires to use the catheter, the user removes sealing covers 222 and 223. Next, the user removes the catheter from the compartment 213a. The user then inserts the catheter into the compartment 213b making sure to insert the tube 214 into the lumen of the sleeve 220. After fully inserting the tube 214 into the sleeve 220 and waiting for a short predetermined time period, i.e., a few seconds to a few minutes (a time period sufficient to allow the coating of the tube 214 to become sufficiently hydrated and/or pre-wetted), the user can remove the catheter from the compartment 213b (while the sleeve 220 remains in the compartment 213b) and then insert the same into the user's (or another user's) body.

As with the previous embodiment, the sleeve 220 contains all or nearly all of the fluid that is arranged in the container 212 and can be placed in direct contact with a coating of the tube 214. The funnel 217 can remain in a dry state in a non-fluid containing space 213a of the package 212.

In embodiments, the package 212 is made of foil material which ensures that the catheter assembly and the sleeve 220 are not contaminated. The package 212 also ensures that its contents are sealed in a gas and/or fluid tight and/or impermeable manner so that hydrating fluid will not leak out. In embodiments, at least an inner layer, i.e., the layer in contact with the sleeve 220, of the package 212 is made of a foil material. In embodiments, the package 212 is made of a single layer foil material. In embodiments, the package 212 is made of plural layers of different materials with at least one layer being a foil material.

In embodiments, the caps 222 and 223 are optional. These can, in embodiments, be formed by sealing the ends of the package (after inserting the catheter members into the package). These ends can then be torn or pealed open. Such an alternative configuration to the caps 222 and 223 would likely be cheaper to manufacture.

In still other embodiments, the material forming the sleeve 220 can be applied to and/or coated onto the material forming the compartment 213b of the package 212 so as to form a package compartment having a fluid absorbing and storing inner liner material. In other embodiments, the material forming the sleeve 220 can be co-extruded with the material forming the compartment 213b of the package 212 so as to form a package having a fluid absorbing and storing inner liner material in compartment 213b. In other embodiments, the material forming the sleeve 220 is laminated with the material forming the compartment 213b of the package 212 so as to form a package compartment 213b having a fluid absorbing and storing inner liner material.

In order to form the assembly package of FIG. 8, in embodiments, a catheter, e.g., of the type shown in FIG. 6, can be inserted into compartment 213a shown in FIG. 8 and then the cap 222 can be installed. A sleeve 220 can be inserted into compartment 213b shown in FIG. 8 and then the cap 223 can be installed. However, prior to installation of the cap 223, the sleeve 220 can be exposed to or immersed in a fluid such as water (which can be poured into the chamber 213b). Since the sleeve 220 is made of a material that can absorb fluid and expand, this causes the sleeve 220 to swell until it reaches a swollen wall thickness. In this swollen state, the sleeve 220 retains the fluid between an inside diameter and an outside diameter. Once the catheter is slid into the sleeve 220 located in the compartment 213b, it can sufficiently hydrate the coating of the tube 214 (after a predetermined amount of time). Furthermore, since the package 212 is fluid impermeable (especially compartment 213b), it ensures that the fluid in the sleeve 220 cannot escape the package 212 or be contaminated with outside the package 212.

In embodiments, the inside diameter of the sleeve 220 is fluid permeable and wets and hydrates the coating of the tube 214 when contacting the tube 214. In embodiments, the outside diameter of the sleeve 220 is also fluid permeable and slightly wets the package 212 when contacting the same. However, unlike the coating of the tube 214, the package 212 does not absorb the fluid. In embodiments, the outside diameter of the sleeve 220 can alternatively and/or additionally be made fluid impermeable so as not to wet the package 212 when contacting the same.

According to another non-limiting embodiment, the hydrating sleeve 220 shown in FIG. 8 can utilize a sleeve configuration of the type shown in FIGS. 4 and 5, i.e., the sleeve 220 can have a hydration containing inner sleeve layer and a foil outer layer.

Figure 9:
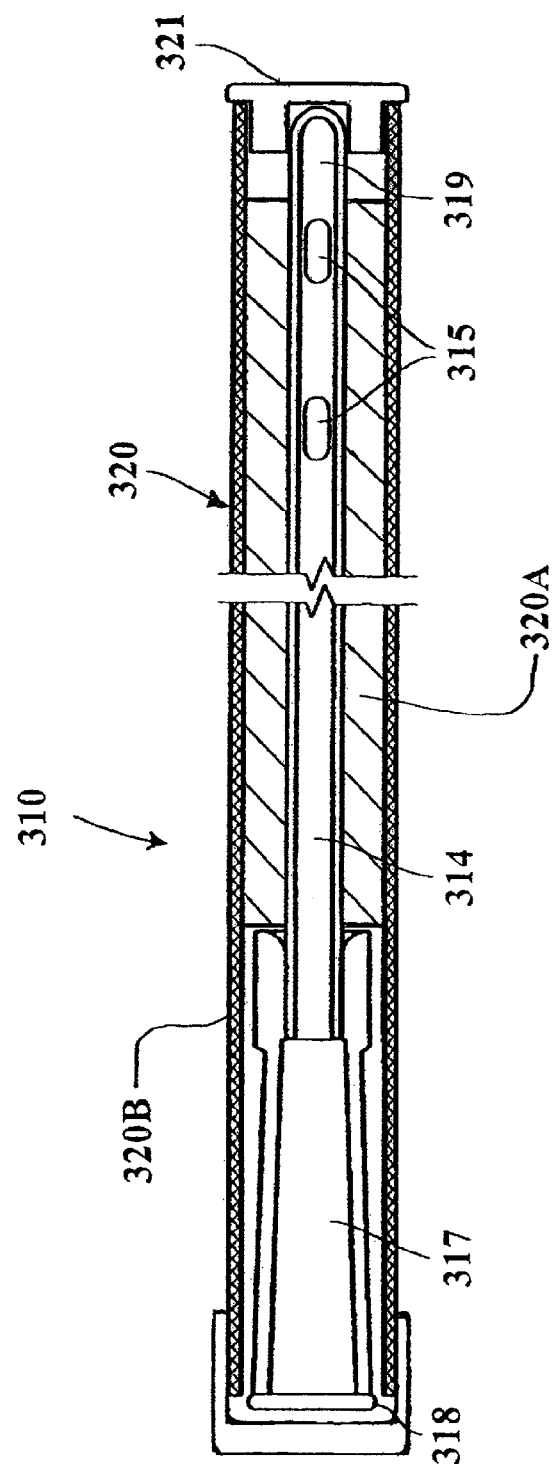
FIG. 9 shows a pre-wetted catheter assembly package in accordance with still another non-limiting embodiment of the invention.

FIG. 9 shows another non-limiting embodiment of a pre-wetted urinary catheter assembly package of the present invention. In FIG. 9, the catheter assembly package is in a storage position and/or prior to use configuration.

The assembly package 310 shown in FIG. 9 includes a catheter assembly arranged within a container which is in the form of an outer sleeve 320B and end cap 321 affixed thereto. An alternative sealing device can also be utilized instead of the end cap 321. The catheter assembly includes a catheter having an insertable elongate tube portion 314, one or more drainage eyelets 315, a funnel 317, a proximal end 318, and a distal end 319. A fluid containing sleeve 320A is arranged in the package sleeve 320B and is positioned over a substantial portion of the tube 314. The sleeve 320A contains all or nearly all of the fluid that is arranged in the container 320B, and is in direct contact with a coating of the tube 314. The funnel 317 remains in a dry state in a non and/or low-fluid containing space of the package 320B. Thus, only the portion of the catheter in contact with the sleeve 320A, i.e., all, nearly all, or most of the tube 314, is wetted or maintained in a pre-wetted state. In embodiments, the sleeve 320A is not non-removably connected to the outer sleeve 320B. In other embodiments, the sleeve 320A may be non-removably connected to the outer sleeve 320B. In this way, the user can slide off the sleeve 320A when the user removes the cap 318, then grips the funnel 317 with one hand and the sleeve 320B with the other hand, and then slides the catheter out of the package 320B (the sleeve 320A remains in the package 320B). Since all or nearly all of the fluid which hydrates the coating of the tube 314 is disposed in the sleeve 320A, removing the catheter will not cause any fluid to spill out of the package 320B when opened. Furthermore, as the sleeve 320A remains in the package 320B, the user need not come into contact with the fluid. Once the catheter is removed from the package 320B, it can be inserted into the user's body while the user grips the funnel 317. As is the case with conventional catheters, the coating of the tube 314 is, in embodiments, a lubricious coating to facilitate insertion of the catheter into the user's body.

In order to form the assembly package of FIG. 9, in embodiments, a catheter, e.g., of the type shown in FIG. 6, can be inserted into a fluid containing sleeve 320A shown in FIG. 9 which is already arranged within an outer sleeve 320B. Prior to or after insertion of the sleeve 320A into the sleeve 320B, the sleeve 320A can be exposed to or immersed in a fluid such as water. Since the sleeve 320A is made of a material that can absorb fluid and expand, this causes the sleeve 320A to swell until it reaches a swollen wall thickness. In this swollen state, the sleeve 320A retains the fluid between an inside diameter and an outside diameter. Once the catheter is slid into the sleeve 320A, it can maintain the coating of the tube 314 is a hydrated state. Alternatively, the sleeve 320A can be slid onto the catheter tube 314 and then exposed to a hydrating fluid. This sub-assembly can then be slid into the sleeve package 320B.

Since the sleeve package 320B is fluid impermeable, it ensures that the fluid in the sleeve 320A cannot escape the package 320B or be contaminated with outside the package. In embodiments, the inside diameter of the sleeve 320A is fluid permeable and wets and hydrates the coating of the tube 314 when contacting the tube 314. In embodiments, the outside diameter of the sleeve 320A is also fluid permeable and slightly wets the sleeve package 320B when contacting the same. However, unlike the coating of the tube 314, the package 320B does not absorb the fluid. In embodiments, the outside diameter can alternatively be made fluid impermeable so as not to wet the package 320B when contacting the same. A removable cap 318 is arranged on one end of the sleeve 320B in order to prevent contact with the funnel 317 and to seal off the distal end of the sleeve package 320B.

In embodiments, the package 312B is made of foil material for protecting the catheter assembly and the sleeve 320A. The foil functions as a moisture barrier to prevent evaporation of water from the fluid hydrating the sleeve through the package and properly seals the same within the package. The package 312B (when its ends are covered with caps 318 and 321 or otherwise sealed) also ensures that its contents are enclosed in a gas and/or fluid tight and/or impermeable manner so that hydrating fluid will not leak out. In embodiments, at least an inner layer, i.e., the layer in contact with the sleeve 320, of the package 312B is made of a foil material. In embodiments, the package 312B is made of a single layer foil material. In embodiments, the package 312B is made of plural layers of different materials with at least one layer being a foil material.

According to another non-limiting embodiment, the hydrating sleeve 320A shown in FIG. 9 can utilize a sleeve configuration of the type shown in FIGS. 4 and 5, i.e., the sleeve 320A can have a hydration containing inner sleeve layer and a foil outer layer which may or may not be secured to an inner cylindrical surface of the sleeve 320B.

Figure 10:
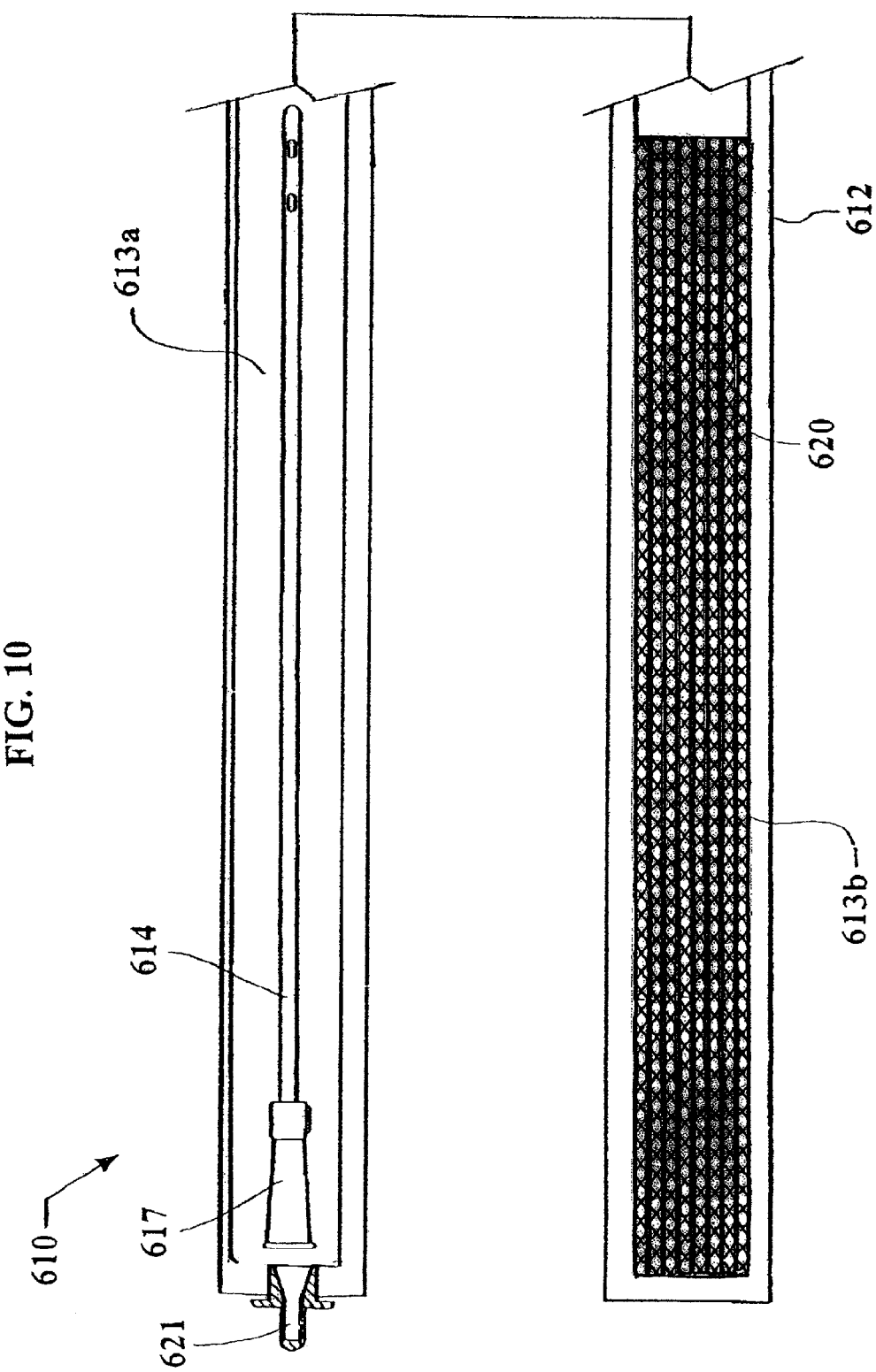
FIGS. 10 and 11 show a pre-wetted catheter assembly package in accordance with still another non-limiting embodiment of the invention.
Figure 11:
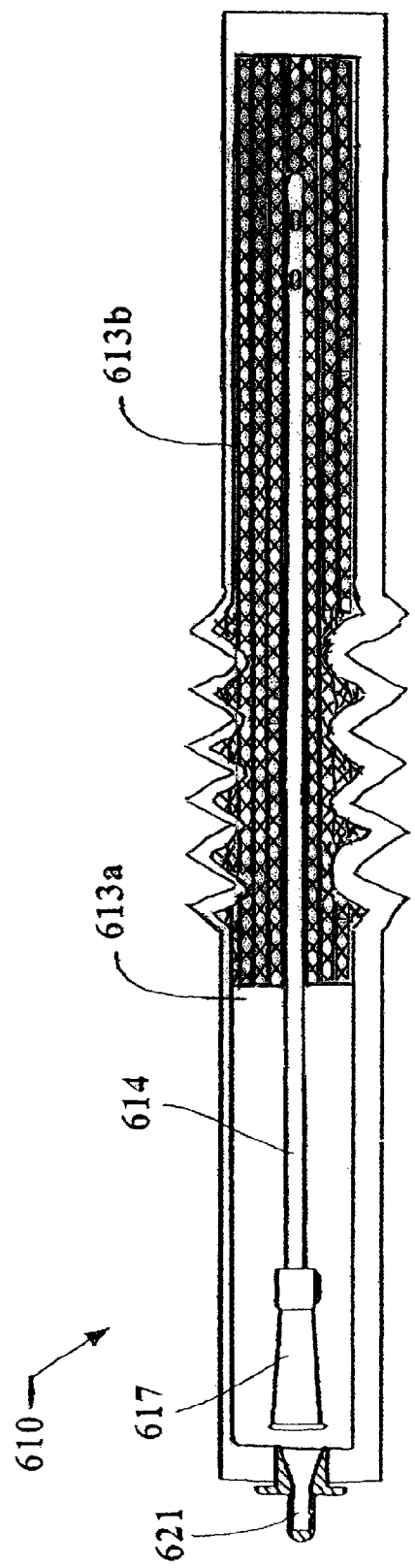

FIGS. 10 and 11 show another non-limiting embodiment of a pre-wetted urinary catheter of the present invention. FIG. 10 shows the catheter assembly package in a storage position and/or prior to use configuration. FIG. 11 shows the catheter assembly package in a position just prior to use.

The assembly package 610 shown in FIG. 11 includes a catheter arranged within a first compartment 613a of a flexible container 612 which can be in the form of a package such as the type shown in FIG. 2, but having a more elongate configuration. A fluid containing inner layer (or sleeve) 620 is arranged within a second compartment 613b of the container 612. The catheter has an insertable elongate tube portion 614, one or more drainage eyelets, a funnel 617 arranged on a proximal end, and a distal end. The fluid containing sleeve 620 is sized to be positioned over a substantial portion of the tube 614. When the user desires to use the catheter, the user manipulates the package 610 so that the catheter can be inserted into the sleeve 620 (see FIG. 11). Then, he can remove sealing cover or cap 621 (or otherwise unseal an end of the package) and remove the catheter from the compartment 613a. However, before the catheter is removed from the package 612, the tube 614 must be fully inserted into the sleeve 620 for a short predetermined time period (and retained in the configuration shown in FIG. 11). This time period can be, e.g., a few seconds to a few minutes and is, in embodiments, a time period sufficient to allow the coating of the tube 614 to become sufficiently hydrated and/or pre-wetted. As with the previous embodiment, the sleeve 620 contains all or nearly all of the fluid that is arranged in the container 612 and can be placed in direct contact with a coating of the tube 614. Prior to use, the funnel 617 and tube 614 remains in a dry state in a non-fluid containing space 613a of the package 612 (as shown in FIG. 10). Thus, catheter is not maintained in a pre-wetted state until it assumes the position shown in FIG. 11. In embodiments, the inner layer or sleeve 620 is not removable from the package 612 with the catheter and/or is secured or affixed to an inner surface of the package 612. Alternatively, it is possible to seal the package 612 between portion 613a and portion 613b with, e.g., a light "V" seal. The user could then push the member 614 through the seal into portion 613b having the hydration sleeve or material 620. Once removed from the package 612, the user can grip the funnel 617 with one hand and the package 612 with the other hand, and then slide the catheter out of the compartment 613a. Since all or nearly all of the fluid which hydrates the coating of the tube 614 is disposed in the inner layer or sleeve 620, removing the catheter assembly from the package 612 will not cause any fluid to spill out of the package 612 when opened. Furthermore, if the sleeve 620 is gripped from outside the package 612 and is retained in the compartment 613b, the user need not come into contact with the fluid. Once the catheter is properly hydrated while in the package 612, it can be removed therefrom and inserted into the user's body while the user grips the funnel 617. As is the case with conventional catheters, the coating of the tube 614 is, in embodiments, a lubricious coating to facilitate insertion of the catheter into the user's body.

In order to form the assembly package of FIG. 10, in embodiments, an inner material or sleeve 620 can be inserted into compartment 613b shown in FIG. 10, then a catheter can be inserted into compartment 613a shown in FIG. 10. Then, the cap 621 can be installed or alternatively the package can be otherwise sealed. However, prior to insertion into the package 612, the sleeve 620 can be exposed to or immersed in a fluid such as water. Since the sleeve 620 is made of a material that can absorb fluid and expand, this causes the sleeve 620 to swell until it reaches a swollen wall thickness. In this swollen state, the sleeve 620 retains the fluid between an inside diameter and an outside diameter. Once the catheter is slid into the sleeve 620 (as shown in FIG. 11), it can hydrate the coating of the tube 614. Furthermore, since the package 612 is fluid impermeable, it ensures that the fluid in the sleeve 620 cannot escape the package 612 or be contaminated with outside the package 612. In embodiments, the inside diameter (if and when the material 620 is deformed into a circular shape) of the sleeve 620 is fluid permeable and wets and hydrates the coating of the tube 614 when contacting the tube 614. In embodiments, the outside diameter of the sleeve 620 is also fluid permeable and slightly wets the package 612 when contacting the same. However, unlike the coating of the tube 614, the package 612 does not absorb the fluid. In embodiments, the outside diameter can alternatively be made fluid impermeable so as not to wet the package 612 when contacting the same.

In embodiments, the package 612 is made of foil material which ensures that the catheter assembly and the sleeve 620 are not contaminated. The package 612 (when it end is covered with cap 621) also ensures that its contents are sealed in a gas and/or fluid tight and/or impermeable manner so that hydrating fluid will not leak out. In embodiments, at least an inner layer, i.e., the layer in contact with the sleeve 620, of the package 612 is made of a foil material. In embodiments, the package 612 is made of a single layer foil material. In embodiments, the package 612 is made of plural layers of different materials with at least one layer being a foil material.

According to another non-limiting embodiment, the hydrating material or sleeve 620 shown in FIG. 10 can utilize a sleeve configuration of the type shown in FIGS. 4 and 5, i.e., the material or sleeve 620 can have a hydration containing inner sleeve layer and a foil outer layer which may or may not be secured to an inner surface of the package 612.

In each of the herein disclosed embodiments, the fluid containing member or sleeve may, in embodiments, be a hydrogel sleeve. In embodiments, the fluid containing member may also have at least one of the following: a wall thickness T that is 1/16 inch or greater, e.g., 1/8 inch, (in a fully hydrated condition); may be generally cylindrical; may also be structured and arranged to maintain a coating of the elongate member in a hydrated condition; may be a tube having an inside diameter sized to receive therein the elongate member; may comprise an extruded polyurethane tube; may comprise one or more materials described above; may comprise a material which swells when exposed to a fluid and which absorbs and retains fluid in a wall between an inner diameter and an outer diameter; may be structured and arranged to swell when exposed to a fluid; may be structured and arranged to swell when exposed to water; may be structured and arranged, in embodiments, to absorb about 90% of its weight in fluid; may be structured and arranged to absorb about 90% of its weight in water; and may comprise a hydrated polyurethane tube.

The catheter insertion tube member and hydrating sleeve may have a round cross-sectional shape, an oval cross-sectional shape, or any other cross-sectional shape that may facilitate insertion into the body of a user/patient, and, in particular, into the bladder of the user/patient through the urethra. The catheter insertion member in accordance with various embodiments) can preferably contain a biocompatible hydrophilic coating on at least an outer surface thereof. The coating may also have antimicrobial properties and/or contain antimicrobial agents. Suitable non-limiting examples of such lubricious and antimicrobial coatings are disclosed in U.S. Pat. Nos. 4,585,666; 5,558,900; 5,077,352; 5,179,174; 6,329,488 (suitable for, e.g., polysiloxane substrates); U.S. Pat. Nos. 6,716,895; 6,949,598; 7,179,849, and, WO 2007/050685, each of which is incorporated by reference in its entirety.

The antimicrobial agent used on the catheter may be one listed in an over the counter (OTC) monograph. Biocompatible coatings conform with the following tests: mucosal irritation, sensitization, cytotoxicity, acute systemic toxicity, and implantation. ("Tripartite Biocompatibility Guidance for Medical Devices," DSMA (Apr. 24, 1987) (Updated May 21, 1996)). The purpose of the wetting fluid is to maintain hydration of the lubricious coating such that upon insertion of the conduit into a user, at least an outer portion thereof is extremely slippery, facilitating insertion.

The catheter insertion member may preferably be constructed from a suitable polymeric material, such as polyvinyl chloride (PVC), silicone, latex or other synthetic rubber. The components of the catheter disclosed herein can also be made from various well-known materials. For example, the portions of the assembly other than the catheter insertion member can be made of polyvinyl propylene, polyvinyl chloride, polyethylene, polypropylene, and other types of suitable polymeric materials. The components can be molded or extruded according to well-known manufacturing techniques.

Materials commonly used to make the catheter insertion member include, but are not limited to natural rubber latexes (available, for example, from Guthrie, Inc., Tucson, Ariz.; Firestone, Inc., Akron, Ohio; and Centrotrade USA, Virginia Beach, Va.), silicones (available, for example, from GE Silicones, Waterford, N.Y., Wacker Silicones, Adrian, Mich.; and Dow Corning, Inc., Midland, Mich.), polyvinyl chlorides (available, for example, from Kaneka Corp., Inc., New York, N.Y.), polyurethanes (available, for example, from Bayer, Inc., Toronto, Ontario, Rohm & Haas Company, Philadelphia, Pa.; and Ortec, Inc., Greenville, S.C.), plastisols (available, for example, from G S Industries, Bassett, Va.), polyvinyl acetate, (available, for example from Acetex Corp., Vancouver, British Columbia) polyacrylates (available, for example, from Rohm and Haas, Philadelphia, Pa.) and methacrylate copolymers (available, for example, from Heveatex, Inc., Fall River, Mass.). Synthetic and natural rubber latexes, polyurethanes, and silicones are preferred materials. Any combination of the foregoing materials may also be used in making catheters such as are used to produce latex Foley catheters.

The urinary catheter, and in particular, the insertion member thereof, of the present invention can be manufactured by a variety of well-known methods. The tubing can be extruded and the funnel injection molded and then attached to the desired length of tubing. The tip of the tube can then be closed and rounded by thermoforming (for example, for PVC tubes) or molded (for example, for silicone tubes). Eye holes can then be punched or otherwise formed near the tip of the distal end of the tube to provide an outlet for urine drainage thru the tube when it is inserted into a bladder. Alternatively, the entire catheter can be fabricated by dip molding. In this procedure, an elongated rod or "form" is dipped into a liquid coating material such as synthetic or natural rubber latex, for example, to form a layer of material on the form. The deposition of material can be increased by first dipping the form into a coagulant solution to coat the form with a film of chemical that causes the latex to coagulate onto the form. Calcium nitrate is commonly used as the coagulant, and other additives may be used to enhance the removal of the tube from the form once the catheter is formed and dried. The form has the shape and dimensions of the lumen of the catheter. The catheter may be formed from a single dip coating of the form or by multiple coating layers. When a suitable material thickness is achieved on a form, the forms are dried to produce the catheter. If multiple coatings are used to form the catheter, each coating may be dried before the next is applied. Once dried, the catheter may be stripped from the form. The catheters may then be washed and dried, and eyelets may then be formed thereon. Further manufacturing steps may be found in U.S. 2004/0133156, the disclosure of which is incorporated by reference herein.

The catheter insertion member may preferably be in the range of about 8 cm to about 18 cm, and, it may have an elliptical cross-sectional shape similar to the shape of the male urethra. Different lengths, sizes (e.g., diameter, width, etc.), and configurations are possible for the catheter, depending on the user's anatomy. For female users, the insertable length may range from 40 to 100 mm, for example 50 to 80 mm, such as 55 to 75 mm. For male users, the insertable length can range from 170 to 260 mm, such as 190 to 240 mm, for example 230 mm. The tip design can vary according to the needs of a user, for example, the catheters disclosed herein can be provided with a coude tip. The catheter may have a round or substantially round cross-sectional shape, an oval cross-sectional shape, or any other cross-sectional shape that may facilitate insertion into the body of a user/patient, and in particular, into the bladder of the user/patient through the urethra. According to various embodiments, the shape of the catheter can also be variable along its length.

This invention has been described and specific examples of the invention have been portrayed. While the invention has been described in terms of particular variations and illustrative figures, those of ordinary skill in the art will recognize that the invention is not limited to the variations of figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A catheter assembly, comprising:
   a catheter including one or more distal drainage openings;
   a coating disposed on an outer surface of the catheter;
   a fluid containing sleeve having a foil outer layer, the fluid containing sleeve configured for positioning over the outer surface of the catheter to maintain the coating in a hydrated state; and
   a container enclosing the catheter and the fluid containing sleeve, wherein substantially all fluid in the container is in the fluid containing sleeve.

2. The catheter assembly according to claim 1, wherein the container includes a foil layer.

3. The catheter assembly according to claim 2, wherein the foil layer is a sole layer of the container.

4. The catheter assembly according to claim 2, wherein the container includes a plurality of layers, the foil layer of the container being an inner layer in contact with the foil outer layer of the fluid containing sleeve.

5. The catheter assembly according to claim 4, wherein the foil layer of the container is secured to the foil outer layer of the fluid containing sleeve.

6. The catheter assembly according to claim 2, wherein the foil layer of the container is generally cylindrical.

7. The catheter assembly according to claim 1, wherein the fluid containing sleeve is structured and arranged to swell when exposed to a fluid.

8. The catheter assembly according to claim 1, wherein the fluid containing sleeve is structured and arranged to absorb about 90% of its weight in fluid.

9. The catheter assembly according to claim 1, wherein the container comprises a sealed package.

10. The catheter assembly according to claim 9, wherein the sealed package is a fluid impermeable package.

11. The catheter assembly according to claim 1, wherein the fluid containing sleeve has a wall thickness that is ⅛ inch or greater.

12. The catheter assembly according to claim 1, wherein the fluid containing sleeve comprises a material selected from the group consisting of a hydrogel, a hydrophilic polymer, an extruded polyurethane, and a polyether polyurethane-urea.

13. The catheter assembly according to claim 1, wherein the fluid containing sleeve comprises a hydrophilic polymer selected from the group consisting of polyethylene oxide, poly vinyl alcohol, carboxy methyl cellulose, hydroxyl ethyl cellulose, hydroxyl ethyl methacrylate, acrylic polymers, and collagen.

14. The catheter assembly according to claim 1, wherein the coating is selected from the group consisting of a hydrateable coating, a lubricious coating, a hydrophilic biocompatible coating, and combinations thereof.

15. The catheter assembly according to claim 1, wherein the fluid containing sleeve is disposed over the catheter in the container, and wherein the catheter is removable from the container without fluid leaking out of the container.

16. The catheter assembly according to claim 15, wherein the fluid containing sleeve is non-removably coupled to the container.

17. The catheter assembly according to claim 15, wherein the catheter is removable from the container along with the fluid containing sleeve.

18. The catheter assembly according to claim 1, wherein the catheter includes a funnel at a proximal end therof.

19. The catheter assembly according to claim 1, wherein the fluid containing sleeve comprises a gripping end which does not contain fluid and allows a user to grip the fluid containing sleeve without fingers of the user becoming exposed to fluid.

20. The catheter assembly according to claim 1, wherein the container comprises a first compartment containing the catheter and a second compartment containing the fluid containing sleeve.

21. The catheter assembly according to claim 20, wherein the catheter is removable from the first compartment and insertable into the fluid containing sleeve in the second compartment.

22. The catheter assembly according to claim 21, further comprising a first removable cover or openable section allowing a user to access and remove the catheter from the first compartment, and a second removable cover or openable section allowing the user to insert the catheter into the second compartment.

23. The catheter assembly according to claim 1, wherein the container comprises a single flexible compartment which encloses the catheter and the fluid containing sleeve while axially separated from each other and is configured to allow a user to position the catheter into the fluid containing sleeve while the catheter and the fluid containing sleeve remain enclosed within the single flexible compartment.

* * * * *